United States Patent
Fuller et al.

(10) Patent No.: US 12,290,642 B2
(45) Date of Patent: May 6, 2025

(54) GUIDE EXTENSION CATHETER

(71) Applicant: BOSTON SCIENTIFIC SCIMED, INC., Maple Grove, MN (US)

(72) Inventors: Jeffrey Steven Fuller, Brooklyn Park, MN (US); Soo-Young Yoon, Maple Grove, MN (US); Louis Warner Stefanich, Minneapolis, MN (US); John E. Uschold, North Branch, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/380,705

(22) Filed: Oct. 17, 2023

(65) Prior Publication Data
US 2024/0042169 A1 Feb. 8, 2024

Related U.S. Application Data

(63) Continuation of application No. 16/723,519, filed on Dec. 20, 2019, now Pat. No. 11,826,517, which is a
(Continued)

(51) Int. Cl.
*A61M 25/00* (2006.01)
*A61M 25/01* (2006.01)
(Continued)

(52) U.S. Cl.
CPC .... *A61M 25/0023* (2013.01); *A61M 25/0014* (2013.01); *A61M 25/0045* (2013.01);
(Continued)

(58) Field of Classification Search
CPC .......... A61M 25/0023; A61M 25/0014; A61M 25/0045; A61M 25/0662; A61M 25/10;
(Continued)

(56) References Cited

U.S. PATENT DOCUMENTS

| 4,564,014 A | 1/1986 | Fogarty et al. |
| 4,616,652 A | 10/1986 | Simpson |

(Continued)

FOREIGN PATENT DOCUMENTS

| AU | 2013290294 A1 | 1/2014 |
| AU | 2013296736 B2 | 2/2015 |

(Continued)

OTHER PUBLICATIONS

International Search Report and Written Opinion dated Jan. 18, 2019 for International Application No. PCT/US2017/057278.
(Continued)

*Primary Examiner* — Theodore J Stigell
(74) *Attorney, Agent, or Firm* — Seager, Tufte & Wickhem, LLP

(57) ABSTRACT

Medical devices and methods for making and using medical devices are disclosed. An example medical device may include a guide extension catheter. The guide extension catheter may include a proximal member having a proximal end, a distal end, and a proximal diameter. The guide extension catheter may additionally include a collar member attached to an extension portion of the proximal member, where the extension portion may be located at the distal end of the proximal member. The extension portion may allow a delivery device to be inserted through the guide extension catheter to extend along a surface of the extension portion and align with a lumen of a distal sheath of the guide extension catheter.

17 Claims, 13 Drawing Sheets

Related U.S. Application Data continuation of application No. 15/787,678, filed on Oct. 18, 2017, now Pat. No. 10,537,709.

(60) Provisional application No. 62/409,603, filed on Oct. 18, 2016.

(51) Int. Cl.
*A61M 25/06* (2006.01)
*A61M 25/10* (2013.01)

(52) U.S. Cl.
CPC ........ *A61M 25/0662* (2013.01); *A61M 25/10* (2013.01); *A61M 2025/0004* (2013.01); *A61M 2025/0046* (2013.01); *A61M 25/0108* (2013.01); *A61M 2025/0175* (2013.01)

(58) Field of Classification Search
CPC ...... A61M 25/0108; A61M 2025/0004; A61M 2025/0046; A61M 2025/0175
See application file for complete search history.

(56) References Cited

U.S. PATENT DOCUMENTS

| | | |
|---|---|---|
| 4,762,129 A | 8/1988 | Bonzel |
| 5,102,402 A | 4/1992 | Dror et al. |
| 5,106,455 A | 4/1992 | Jacobsen et al. |
| 5,120,323 A | 6/1992 | Shockey et al. |
| 5,232,445 A | 8/1993 | Bonzel |
| 5,238,004 A | 8/1993 | Satjian et al. |
| 5,257,974 A | 11/1993 | Cox |
| 5,267,982 A | 12/1993 | Sylvanowicz |
| 5,338,300 A | 8/1994 | Cox |
| 5,370,615 A | 12/1994 | Johnson |
| 5,374,286 A | 12/1994 | Morris |
| 5,385,562 A | 1/1995 | Adams et al. |
| 5,387,193 A | 2/1995 | Miraki |
| 5,415,639 A | 5/1995 | Vandeneinde et al. |
| 5,441,489 A | 8/1995 | Utsumi et al. |
| 5,458,584 A | 10/1995 | Ginn et al. |
| 5,484,407 A | 1/1996 | Osypka |
| 5,525,974 A | 6/1996 | Matai |
| 5,527,292 A | 6/1996 | Adams et al. |
| 5,613,948 A | 3/1997 | Avellanet |
| 5,636,634 A | 6/1997 | Kordis et al. |
| 5,637,090 A | 6/1997 | Mcgee et al. |
| 5,662,606 A | 9/1997 | Cimino et al. |
| 5,738,667 A | 4/1998 | Solar |
| 5,772,609 A | 6/1998 | Ngyuen et al. |
| 5,928,191 A | 7/1999 | Houser et al. |
| 6,007,522 A | 12/1999 | Agro et al. |
| 6,059,748 A | 5/2000 | Teirstein et al. |
| 6,066,126 A | 5/2000 | Li et al. |
| 6,139,510 A | 10/2000 | Palermo |
| 6,143,002 A | 11/2000 | Vietmeir |
| 6,152,944 A | 11/2000 | Holman et al. |
| 6,159,195 A | 12/2000 | Ha et al. |
| 6,273,850 B1 | 8/2001 | Gambale et al. |
| 6,290,693 B1 | 9/2001 | Jung et al. |
| 6,364,900 B1 | 4/2002 | Heuser |
| 6,508,803 B1 | 1/2003 | Horikawa et al. |
| 6,511,470 B1 | 1/2003 | Hamilton |
| 6,537,294 B1 | 3/2003 | Boyle et al. |
| 6,544,215 B1 | 4/2003 | Bencini et al. |
| 6,575,958 B1 | 6/2003 | Happ et al. |
| 6,579,246 B2 | 6/2003 | Jacobsen et al. |
| 6,613,075 B1 | 9/2003 | Healy et al. |
| 6,623,268 B2 | 9/2003 | Diamond et al. |
| 6,638,268 B2 | 10/2003 | Niazi |
| 6,695,793 B2 | 2/2004 | Brennan et al. |
| 6,746,422 B1 | 6/2004 | Noriega et al. |
| 6,766,720 B1 | 7/2004 | Jacobsen et al. |
| 6,866,655 B2 | 3/2005 | Hackett |
| 6,953,454 B2 | 10/2005 | Peterson et al. |
| 6,979,319 B2 | 12/2005 | Manning et al. |
| 7,074,235 B1 | 7/2006 | Roy |
| 7,232,452 B2 | 6/2007 | Adams et al. |
| 7,241,273 B2 | 7/2007 | Maguire et al. |
| 7,294,121 B2 | 11/2007 | Kawata et al. |
| 7,294,124 B2 | 11/2007 | Eidenschink |
| 7,309,334 B2 | 12/2007 | von Hoffmann |
| 7,316,678 B2 | 1/2008 | Nash et al. |
| 7,354,428 B1 | 4/2008 | Gosiengfiao et al. |
| 7,604,612 B2 | 10/2009 | Ressemann et al. |
| 7,717,899 B2 | 5/2010 | Bowe et al. |
| 7,736,355 B2 | 6/2010 | Itou et al. |
| 7,762,984 B2 * | 7/2010 | Kumoyama ...... A61M 25/0023 604/525 |
| 7,892,215 B2 | 2/2011 | Melsheimer et al. |
| 8,048,032 B2 | 11/2011 | Root et al. |
| 8,142,412 B2 | 3/2012 | Hehrlein et al. |
| 8,142,413 B2 | 3/2012 | Root et al. |
| 8,292,850 B2 | 10/2012 | Root et al. |
| 8,298,178 B2 | 10/2012 | Carrillo et al. |
| 8,465,456 B2 | 6/2013 | Stivland |
| 8,996,095 B2 | 3/2015 | Anderson et al. |
| 9,017,309 B2 | 4/2015 | Tanikawa et al. |
| 9,023,093 B2 | 5/2015 | Pal |
| 9,144,662 B2 | 9/2015 | Di Caprio et al. |
| RE45,760 E | 10/2015 | Root et al. |
| RE45,776 E | 10/2015 | Root et al. |
| 9,320,508 B2 | 4/2016 | Carroux |
| 9,352,123 B2 | 5/2016 | Zhou et al. |
| 9,486,611 B2 | 11/2016 | Peterson et al. |
| 9,522,254 B2 | 12/2016 | Belson |
| 9,561,345 B2 | 2/2017 | Garrison et al. |
| 9,616,201 B2 | 4/2017 | Belson |
| 9,675,784 B2 | 6/2017 | Belson |
| 9,681,882 B2 | 6/2017 | Garrison et al. |
| 9,757,540 B2 | 9/2017 | Belson |
| 9,993,613 B2 | 6/2018 | Wang et al. |
| 10,124,147 B2 | 11/2018 | Anderson et al. |
| 10,124,148 B2 | 11/2018 | Falk et al. |
| 11,826,517 B2 * | 11/2023 | Fuller .............. A61M 25/0023 |
| 2001/0018574 A1 | 8/2001 | Toledo et al. |
| 2002/0120320 A1 | 8/2002 | Wang et al. |
| 2002/0128677 A1 | 9/2002 | Duerig et al. |
| 2002/0165574 A1 | 11/2002 | Ressemann et al. |
| 2002/0165598 A1 | 11/2002 | Wahr et al. |
| 2002/0165605 A1 | 11/2002 | Penn et al. |
| 2003/0004537 A1 | 1/2003 | Boyle et al. |
| 2003/0023229 A1 | 1/2003 | Kramer |
| 2003/0050600 A1 | 3/2003 | Ressemann et al. |
| 2003/0069522 A1 | 4/2003 | Jacobsen et al. |
| 2003/0100849 A1 | 5/2003 | Jang |
| 2003/0144657 A1 | 7/2003 | Bowe et al. |
| 2003/0199849 A1 | 10/2003 | Hackett |
| 2004/0059179 A1 | 3/2004 | Maguire et al. |
| 2004/0064089 A1 | 4/2004 | Kesten et al. |
| 2004/0073250 A1 | 4/2004 | Pederson, Jr. et al. |
| 2004/0097904 A1 | 5/2004 | Carrillo et al. |
| 2004/0116832 A1 | 6/2004 | Friedrich et al. |
| 2004/0116848 A1 | 6/2004 | Gardeski et al. |
| 2004/0181174 A2 | 9/2004 | Davis et al. |
| 2004/0186507 A1 | 9/2004 | Hall et al. |
| 2004/0236215 A1 | 11/2004 | Mihara et al. |
| 2005/0033136 A1 | 2/2005 | Govari et al. |
| 2005/0065437 A1 | 3/2005 | Weber et al. |
| 2005/0070844 A1 | 3/2005 | Chow et al. |
| 2005/0080430 A1 | 4/2005 | Wright et al. |
| 2005/0107817 A1 | 5/2005 | White et al. |
| 2005/0148866 A1 | 7/2005 | Gunderson |
| 2005/0234427 A1 | 10/2005 | Eder |
| 2005/0267442 A1 | 12/2005 | Von Oepen |
| 2005/0288730 A1 | 12/2005 | Deem et al. |
| 2006/0030876 A1 | 2/2006 | Peacock et al. |
| 2006/0063973 A1 | 3/2006 | Makower et al. |
| 2006/0069381 A1 | 3/2006 | Itou et al. |
| 2006/0079859 A1 | 4/2006 | Elkins et al. |
| 2006/0173475 A1 | 8/2006 | Lafontaine et al. |
| 2006/0182873 A1 | 8/2006 | Klisch et al. |
| 2006/0189922 A1 | 8/2006 | Amarasinghe et al. |
| 2006/0235458 A1 | 10/2006 | Belson |
| 2006/0259117 A1 | 11/2006 | Pal |

(56) References Cited

U.S. PATENT DOCUMENTS

| | | |
|---|---|---|
| 2006/0282041 A1 | 12/2006 | Melsheimer et al. |
| 2007/0093781 A1 | 4/2007 | Kugler et al. |
| 2007/0114211 A1 | 5/2007 | Reynolds et al. |
| 2007/0260219 A1 | 11/2007 | Root et al. |
| 2007/0299367 A1 | 12/2007 | Melsheimer et al. |
| 2008/0051760 A1 | 2/2008 | Schoenle et al. |
| 2008/0125752 A1 | 5/2008 | Gunderson et al. |
| 2008/0167628 A1 | 7/2008 | Li et al. |
| 2008/0181174 A1 | 7/2008 | Cho |
| 2008/0243065 A1 | 10/2008 | Rottenberg et al. |
| 2009/0005757 A1 | 1/2009 | Taber |
| 2009/0099550 A1 | 4/2009 | Carrillo et al. |
| 2009/0105638 A1 | 4/2009 | Partlett et al. |
| 2009/0177120 A1 | 7/2009 | Tockman et al. |
| 2009/0182412 A1 | 7/2009 | Tan et al. |
| 2009/0264865 A1 | 10/2009 | Kawai |
| 2009/0281399 A1 | 11/2009 | Keel et al. |
| 2009/0319037 A1 | 12/2009 | Rowe et al. |
| 2010/0010475 A1 | 1/2010 | Teirstein et al. |
| 2010/0030186 A1 | 2/2010 | Stivland |
| 2010/0036312 A1 | 2/2010 | Krolik et al. |
| 2010/0049186 A1 | 2/2010 | Ingle et al. |
| 2010/0057050 A1 | 3/2010 | Webler, Jr. |
| 2010/0152706 A1 | 6/2010 | Morris et al. |
| 2010/0198160 A1 | 8/2010 | Voss |
| 2010/0211050 A1 | 8/2010 | Luther |
| 2010/0217237 A1 | 8/2010 | Itou et al. |
| 2010/0234876 A1 | 9/2010 | Watson |
| 2010/0305475 A1 | 12/2010 | Hinchliffe et al. |
| 2010/0318068 A1 | 12/2010 | Melsheimer |
| 2010/0324482 A1 | 12/2010 | Farnholtz |
| 2010/0324539 A1 | 12/2010 | Lupton |
| 2010/0324567 A1 | 12/2010 | Root et al. |
| 2011/0004087 A1 | 1/2011 | Fish et al. |
| 2011/0004197 A1 | 1/2011 | Sansoucy |
| 2011/0004207 A1 | 1/2011 | Wallace et al. |
| 2011/0066139 A1 | 3/2011 | Winegar |
| 2011/0071539 A1 | 3/2011 | LeVert |
| 2011/0082443 A1 | 4/2011 | Griffin et al. |
| 2011/0112564 A1 | 5/2011 | Wolf |
| 2011/0144677 A1 | 6/2011 | Ward et al. |
| 2011/0160763 A1 | 6/2011 | Ferrera et al. |
| 2011/0160834 A1 | 6/2011 | Aggerholm |
| 2011/0172520 A1 | 7/2011 | Lentz |
| 2011/0224625 A1 | 9/2011 | Flickinger et al. |
| 2011/0265943 A1 | 11/2011 | Rosqueta et al. |
| 2011/0301502 A1 | 12/2011 | Gill |
| 2011/0319926 A1 | 12/2011 | Becking et al. |
| 2012/0029628 A1 | 2/2012 | Rowe |
| 2012/0046575 A1 | 2/2012 | Brown |
| 2012/0150271 A1 | 6/2012 | Fischell et al. |
| 2012/0234876 A1 | 9/2012 | Diamond et al. |
| 2012/0316585 A1 | 12/2012 | Jeffrey et al. |
| 2013/0053766 A1 | 2/2013 | Hollett |
| 2013/0144328 A1 | 6/2013 | Weber et al. |
| 2013/0166701 A1 | 6/2013 | Todorov et al. |
| 2013/0197483 A1 | 8/2013 | Anderson et al. |
| 2013/0237962 A1* | 9/2013 | Kawai ............... A61M 25/0068 604/524 |
| 2014/0005558 A1 | 1/2014 | Gregorich et al. |
| 2014/0012281 A1 | 1/2014 | Wang et al. |
| 2014/0018773 A1* | 1/2014 | Wang .................... A61M 25/04 604/528 |
| 2014/0025004 A1 | 1/2014 | Falk et al. |
| 2014/0025043 A1 | 1/2014 | Wang et al. |
| 2014/0039461 A1 | 2/2014 | Anderson et al. |
| 2014/0052097 A1 | 2/2014 | Peterson et al. |
| 2014/0058275 A1 | 2/2014 | Gregorich et al. |
| 2014/0066789 A1 | 3/2014 | Nishigishi et al. |
| 2014/0081243 A1 | 3/2014 | Zhou et al. |
| 2014/0183670 A1 | 7/2014 | Millett et al. |
| 2014/0236123 A1 | 8/2014 | Birmingham et al. |
| 2014/0249508 A1 | 9/2014 | Wang et al. |
| 2014/0276618 A1 | 9/2014 | Di Caprio et al. |
| 2014/0350414 A1 | 11/2014 | McGowan et al. |
| 2015/0029330 A1 | 1/2015 | Hachiya et al. |
| 2015/0032011 A1 | 1/2015 | McGowen et al. |
| 2015/0151090 A1 | 6/2015 | Sutton et al. |
| 2015/0165175 A1 | 6/2015 | Evard et al. |
| 2015/0297905 A1 | 10/2015 | Greenhut et al. |
| 2015/0342629 A1 | 12/2015 | Schneider |
| 2016/0121080 A1 | 5/2016 | Cottone |
| 2016/0129263 A1 | 5/2016 | Demmer et al. |
| 2016/0346509 A1 | 12/2016 | Anderson et al. |
| 2017/0246423 A2 | 8/2017 | Cottone |
| 2018/0104445 A1 | 4/2018 | Fuller et al. |

FOREIGN PATENT DOCUMENTS

| | | |
|---|---|---|
| CN | 1561240 A | 1/2005 |
| CN | 102510763 A | 6/2012 |
| CN | 104768603 A | 7/2015 |
| CN | 104812420 A | 7/2015 |
| CN | 107921235 A | 4/2018 |
| DE | 6321350 A1 | 1/1988 |
| DE | 3819372 C1 | 1/1990 |
| DE | 4320186 A1 | 12/1994 |
| EP | 0277366 A1 | 10/1988 |
| EP | 0564894 A1 | 10/1993 |
| EP | 0704226 A1 | 4/1996 |
| EP | 0710490 A2 | 5/1996 |
| EP | 0710490 A3 | 12/1996 |
| EP | 1457230 A1 | 9/2004 |
| EP | 1479409 A1 | 11/2004 |
| EP | 1534178 A1 | 6/2005 |
| EP | 1639951 A1 | 3/2006 |
| EP | 1656963 A1 | 5/2006 |
| EP | 1681075 A | 7/2006 |
| EP | 1943973 A1 | 7/2008 |
| EP | 1430925 A1 | 12/2009 |
| EP | 2133114 A1 | 12/2009 |
| EP | 2138200 A1 | 12/2009 |
| JP | H01158936 A | 6/1989 |
| JP | H03118077 A | 5/1991 |
| JP | H06197972 A | 7/1994 |
| JP | H07509379 A | 10/1995 |
| JP | H09511159 A | 11/1997 |
| JP | H11508160 A | 7/1999 |
| JP | 2010017211 A | 1/2001 |
| JP | 2001514921 A | 9/2001 |
| JP | 2002513312 A | 5/2002 |
| JP | 3469236 B2 | 11/2003 |
| JP | 2004525691 A | 8/2004 |
| JP | 2005515797 A | 6/2005 |
| JP | 2005524418 A | 8/2005 |
| JP | 2005535380 A | 11/2005 |
| JP | 2006018315 A | 1/2006 |
| JP | 2006506170 A | 2/2006 |
| JP | 2006087643 A | 4/2006 |
| JP | 2006333762 A | 12/2006 |
| JP | 2007502678 A | 2/2007 |
| JP | 3894224 B2 | 3/2007 |
| JP | 2007521034 A | 8/2007 |
| JP | 2007236632 A | 9/2007 |
| JP | 2008515544 A | 5/2008 |
| JP | 2008142351 A | 6/2008 |
| JP | 2008536640 A | 9/2008 |
| JP | 2008307386 A | 12/2008 |
| JP | 2009504343 A | 2/2009 |
| JP | 2009072294 A | 4/2009 |
| JP | 2010509994 A | 4/2010 |
| JP | 2010524631 A | 7/2010 |
| JP | 2010531670 A | 9/2010 |
| JP | 2011135989 A | 7/2011 |
| JP | 2012501690 A | 1/2012 |
| JP | 2014042645 A | 3/2014 |
| JP | 2014045933 A | 3/2014 |
| JP | 2014147458 A | 8/2014 |
| JP | 2015169464 A | 9/2015 |
| JP | 2015169864 A | 9/2015 |
| WO | 9220397 A1 | 11/1992 |
| WO | 9313827 A1 | 7/1993 |
| WO | 9521652 A1 | 8/1995 |
| WO | 9700641 A1 | 1/1997 |

(56) References Cited

FOREIGN PATENT DOCUMENTS

| | | |
|---|---|---|
| WO | 9839056 A2 | 9/1998 |
| WO | 9908614 A1 | 2/1999 |
| WO | 0141858 A2 | 6/2001 |
| WO | 0141858 A3 | 1/2002 |
| WO | 02070061 A1 | 9/2002 |
| WO | 03037415 A1 | 5/2003 |
| WO | 03049798 A2 | 6/2003 |
| WO | 20040068803 A1 | 1/2004 |
| WO | 2004045699 A1 | 6/2004 |
| WO | 2005014100 A1 | 2/2005 |
| WO | 2005018712 A2 | 3/2005 |
| WO | 2005018728 A2 | 3/2005 |
| WO | 2006041881 A2 | 4/2006 |
| WO | 2006045809 A1 | 5/2006 |
| WO | 2006113866 A2 | 10/2006 |
| WO | 2006113868 A2 | 10/2006 |
| WO | 2006119422 A2 | 11/2006 |
| WO | 2007022383 A2 | 2/2007 |
| WO | 2006119422 A3 | 9/2007 |
| WO | 2007146834 A2 | 12/2007 |
| WO | 2008063621 A2 | 5/2008 |
| WO | 2008120209 A1 | 10/2008 |
| WO | 2008123521 A1 | 10/2008 |
| WO | 2008133808 A1 | 11/2008 |
| WO | 2010028090 A2 | 3/2010 |
| WO | 2011086758 A1 | 7/2011 |
| WO | 20110851180 A2 | 7/2011 |
| WO | 2014011677 A1 | 1/2014 |
| WO | 2014022310 A1 | 2/2014 |
| WO | 2014028898 A2 | 2/2014 |
| WO | 2014037836 A1 | 3/2014 |
| WO | 2014152191 A1 | 9/2014 |
| WO | 2015128791 A1 | 9/2015 |
| WO | 2015011850 A1 | 12/2015 |
| WO | 2016057096 A1 | 4/2016 |
| WO | 2016196161 A1 | 12/2016 |
| WO | 2017019900 A1 | 2/2017 |
| WO | 2017053663 A1 | 3/2017 |
| WO | 2017151988 A1 | 9/2017 |
| WO | 2017178077 A1 | 10/2017 |
| WO | 2017189853 A1 | 11/2017 |

OTHER PUBLICATIONS

International Search Report and Written Opinion dated Aug. 27, 2019 for International Application No. PCT/US2019/034074.
International Search Report and Written Opinion dated Aug. 5, 2016 for International Application No. PCT/US2016/034244.
International Search Report and Written Opinion dated May 20, 2014 for International Application No. PCT/US2014/017728.
International Search Report and Written Opinion dated Dec. 20, 2013 for International Application No. PCT/US2013/060151.
International Search Report and Written Opinion dated Sep. 26, 2013 for International Application No. PCT/US2013/051380.
International Search Report and Written Opinion dated Nov. 15, 2013 for International Application No. PCT/US2013/050930.
International Search Report and Written Opinion dated Sep. 18, 2013 for International Application No. PCT/US2013/049784.
International Search Report and Written Opinion dated Sep. 26, 2013 for International Application No. PCT/US2013/050360.
International Search Report and Written Opinion dated Feb. 18, 2014 for International Application No. PCT/US2013/055457.
International Search Report and Written Opinion dated Feb. 3, 2014 for International Application No. PCT/US2013/024148.
International Search Report and Written Opinion dated May 13, 2013 for International Application No. PCT/US2012/063933.

* cited by examiner

GUIDE EXTENSION CATHETER

CROSS-REFERENCE TO RELATED APPLICATIONS

This application is a continuation of U.S. patent application Ser. No. 16/723,519, filed Dec. 20, 2019, which is a continuation of U.S. patent application Ser. No. 15/787,678, filed Oct. 18, 2017, now U.S. Pat. No. 10,537,709, issued Jan. 21, 2020, which claims the benefit of priority under 35 U.S.C. § 119 to U.S. Provisional Application Ser. No. 62/409,603, filed Oct. 18, 2016, the entirety of which are incorporated herein by reference.

TECHNICAL FIELD

The present disclosure pertains to medical devices, and methods for manufacturing medical devices. More particularly, the present disclosure pertains to elongated intracorporeal medical devices including a guide extension catheter.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. In a first aspect, a guide extension catheter may comprise a proximal member having a proximal outer diameter, a proximal portion, and an extension portion extending from a distal end of the proximal portion to a distal end of the proximal member. The guide extension catheter may further comprise a collar member attached to the extension portion and a distal sheath member attached to the collar member, the distal sheath member having a lumen and a distal outer diameter larger than the proximal outer diameter.

In addition or alternative, and in a second aspect, the extension portion of the proximal member may have a width and a length configured to allow a delivery device to extend along a surface of the extension portion and align with the lumen of the distal sheath member.

In addition or alternatively, and in a third aspect, the extension portion of the proximal member may include a transition region transitioning from the proximal portion to a flattened region of the extension portion. The flattened region may have an extension width greater than the proximal outer diameter and less than the distal outer diameter.

In addition or alternatively, and in a fourth aspect, the transition region may extend to a distal end of the extension portion.

In addition or alternatively, and in a fifth aspect, the flattened region may extend proximally 1.5 millimeters from the distal end of the proximal member.

In addition or alternatively, and in a sixth aspect, the extension portion may extend less than 10 millimeters proximal of a distal end of the proximal member.

In addition or alternatively, and in a seventh aspect, the extension portion may extend less than 6.35 millimeters proximal of a distal end of the proximal member.

In addition or alternatively, and in an eighth aspect, the extension portion may extend less than 3 millimeters from a distal end of the proximal member.

In addition or alternatively, and in a ninth aspect, the extension portion may extend proximally 1.5 millimeters from the distal end of the proximal member.

In addition or alternatively, and in a tenth aspect, the collar member may comprise a base portion and one or more ribs connected to the base portion and extending distally away from the base portion. Further, the extension portion of the proximal member may be attached to the base portion of the collar member.

In addition or alternatively, and an eleventh aspect, the extension portion may extend less than 8.5 millimeters from a proximal end of the collar member.

In addition or alternatively, and in a twelfth aspect, the extension portion may have an arcuate cross-section that mates with the arcuate cross-section of the base portion.

In addition or alternatively, and in a thirteenth aspect, a medical treatment delivery system may comprise a delivery device having a nose extending proximally from a distal end of the delivery device and a medical device location extending proximal from a proximal end of the nose, wherein the nose has a distal end with a length extending between the proximal end and the distal end of the nose. The medical treatment delivery system may further comprise a guide extension catheter comprising a proximal member having a proximal outer diameter, a proximal portion, and an extension portion extending from a distal end of the proximal portion to a distal end of the proximal member. The guide extension catheter may further comprise a distal sheath member axially fixed with respect to the proximal member and extending distally of the proximal member, the distal sheath member having a lumen and a distal outer diameter larger than the proximal outer diameter. The nose of the delivery device may be configured to track a guide wire extending through the lumen of the distal sheath member and align the medical device location of the delivery device with the lumen of the distal sheath member prior to the medical device location of the delivery device advancing to the extension portion of the proximal member.

In addition or alternatively, and in a fourteenth aspect, the nose of the delivery device may have a length that is greater than the length of the extension portion.

In addition or alternatively, and in a fifteenth aspect, the length of the extension portion may be less than 3.5 millimeters.

In addition or alternatively, and in a sixteenth aspect, the delivery device may be a stent delivery catheter and the medical device location may be configured to receive a stent.

In addition or alternatively, and in a seventeenth aspect, the delivery device may be a balloon catheter and the medical device location may include a balloon.

In addition or alternatively, and in an eighteenth aspect, the guide extension catheter may comprise a collar attached to the proximal member and the distal sheath member.

In addition or alternatively, and in a nineteenth aspect, a method for manufacturing a guide extension catheter may comprise flattening an extension portion of a proximal member having a proximal end and a distal end. The method may further include grasping the flattened extension portion and bringing the extension portion into contact with a collar. Yet further, the method may include affixing the extension portion to the collar and attaching a distal sheath member to the collar such that the distal sheath member extends distally of the proximal member and the collar. The extension portion of the proximal member may extend proximally from the distal end of the proximal member and has a length configured to facilitate aligning a delivery catheter with a lumen of the distal sheath member.

In addition or alternatively, and in a twentieth aspect, the method may include flattening a portion of the proximal member that extends between the distal end of the proximal member and a location less than ten millimeters proximal of the distal end of the proximal member.

In addition or alternatively, and in a twenty-first aspect, the method may including stamping the extension portion of the proximal member.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
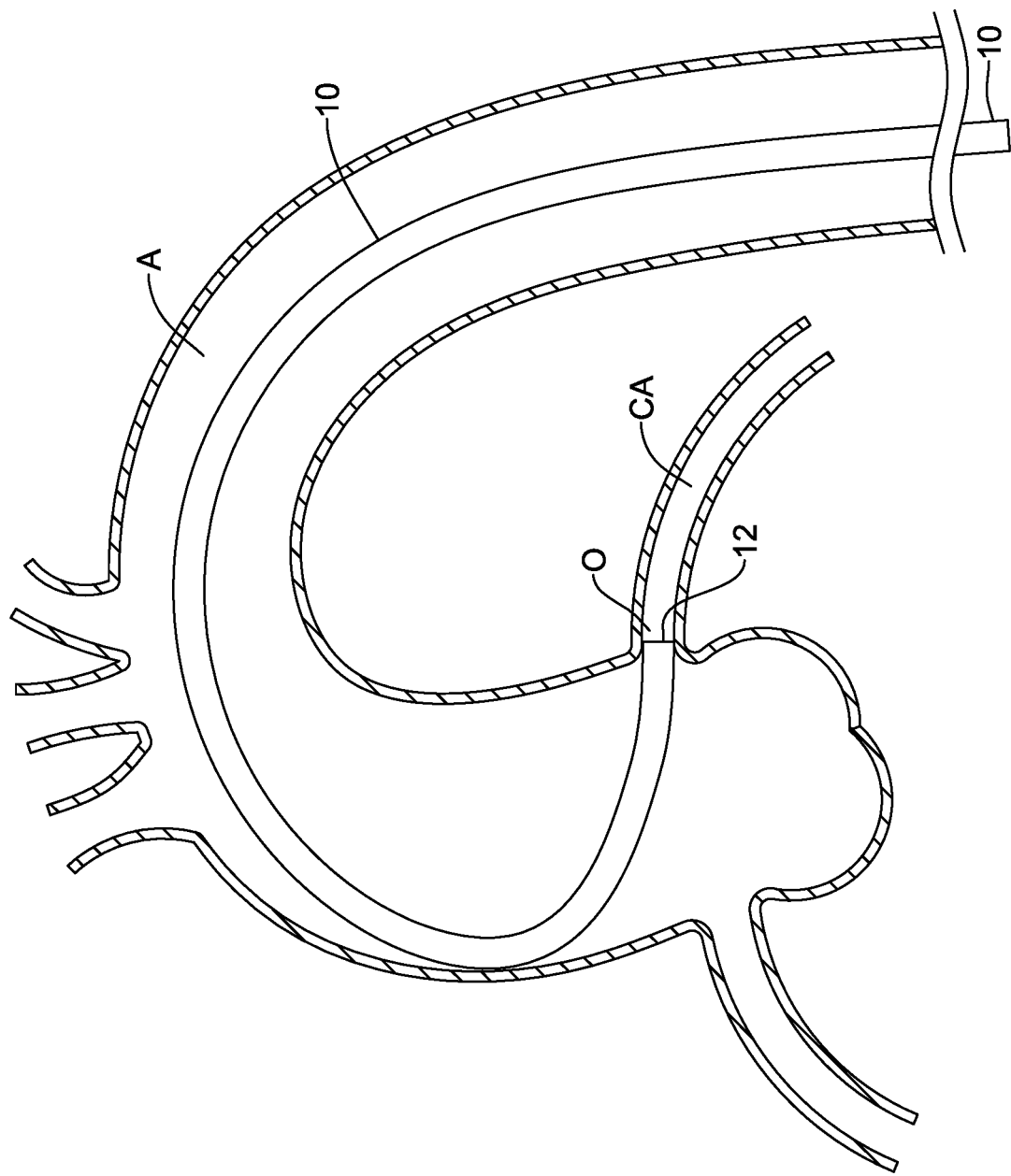
FIG. 1 is a plan view illustrating an example guide catheter advanced through the aorta to the ostium of a coronary artery.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Minimally-invasive cardiac interventions such as percutaneous transluminal coronary angioplasty are widely utilized throughout the world. These procedures may include the use of a guide catheter. For example, a guide catheter 10 may be advanced from a location exterior of vasculature of a patient through a blood vessel such as the aorta A to a position adjacent to the ostium O of a (e.g., left and/or right) coronary artery CA as illustrated in FIG. 1, such that the guide catheter 10 may extend from exterior vasculature of a patient to adjacent the patient's coronary artery when inserted. When so positioned, a delivery device (e.g., a catheter, a balloon catheter, a stent delivery system, etc.) may be advanced through guide catheter 10 and into the coronary artery CA to a target location, such that the delivery device may extend from proximal a proximal end of the guide catheter exterior the patient's vasculature to the target location and the delivery device and/or device thereon may be used to perform an appropriate cardiac intervention at the target location.

In order for the delivery device to efficiently reach the intended target location, maintaining the position of guide catheter 10 at the ostium O of the coronary artery CA may be desirable. For example, given that the heart may be beating during the intervention (and/or other factors), the guide catheter 10 may lose its positioning or otherwise be shifted so that it no longer is positioned to efficiently guide the treatment catheter to the coronary arteries. This may include a distal end 12 of guide catheter 10 being shifted away from the ostium O of the coronary artery CA. Because of the shift away from the ostium O, access to the coronary arteries CA may require repositioning of guide catheter 10 in order to bring the distal end 12 back into engagement with the ostium O of the coronary artery CA.

Figure 2:
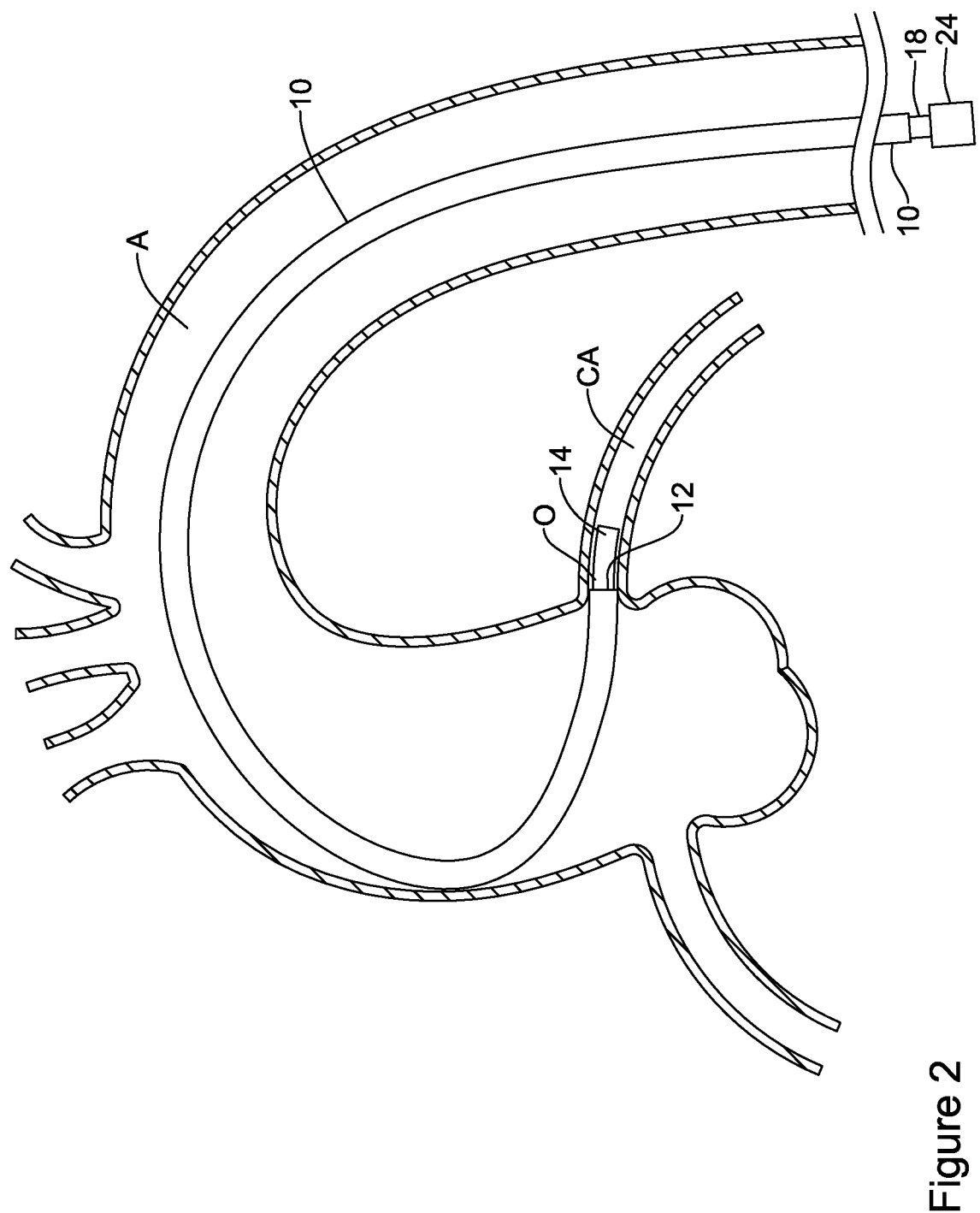
FIG. 2 is a plan view illustrating an example guide extension catheter used in conjunction with a guide catheter.

Disclosed herein are medical devices and methods for making and using medical devices that may improve access to the coronary arteries CA. For example, FIG. 2 illustrates a guide extension catheter 14 extending through guide catheter 10 and beyond distal end 12 of guide catheter 10 into the coronary artery CA. The guide extension catheter 14 (e.g., a proximal portion 18 and a hub 24 of the guide extension catheter 14) may extend from proximal a proximal end of the guide catheter 10 and exterior a patient's vasculature to the coronary artery CA or other target location. Because, for example, the guide extension catheter 14 may extend beyond distal end 12 of guide catheter 10, guide extension catheter 14 may extend beyond the ostium O of the coronary artery CA and into a portion of the coronary artery CA. By extending beyond the ostium O, the guide extension catheter 14 may stabilize the positioning of the guide catheter 10 and allow for improved access to the coronary artery CA for a number of cardiac interventions.

Figure 3:
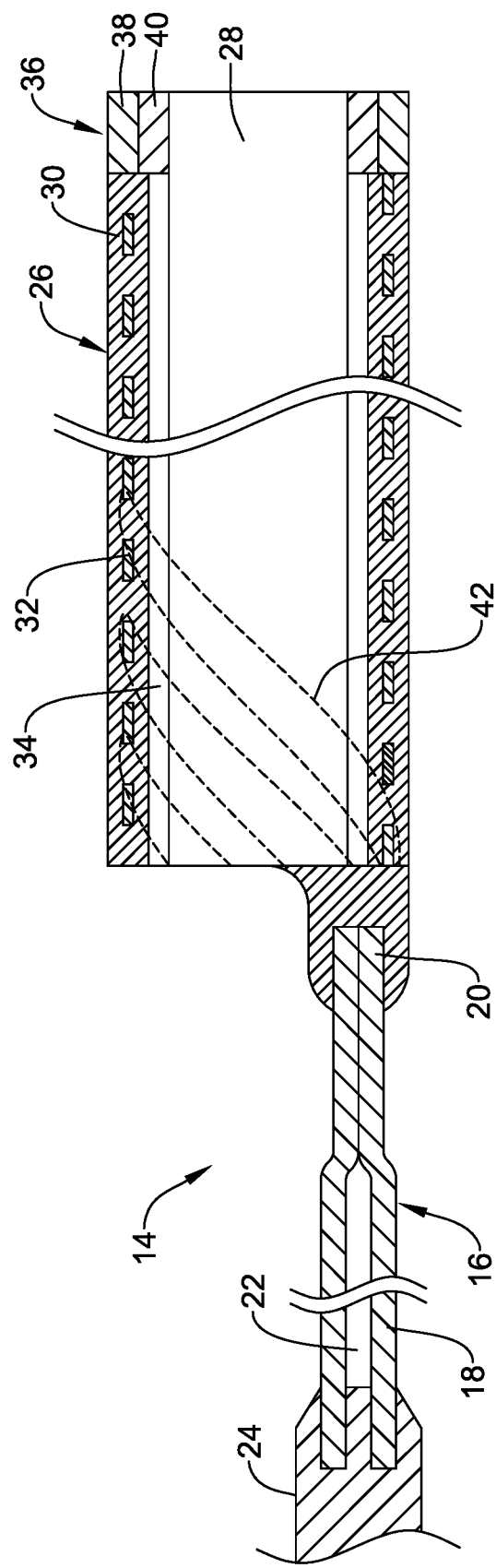
FIG. 3 is a cross-sectional side view of an example guide extension catheter.

FIG. 3 is a cross-sectional side view of guide extension catheter 14. Here it can be seen that guide extension catheter 14 may include a shaft or proximal member 16. Proximal member 16 may include the proximal portion 18 and an extension portion 20 (e.g., a distal portion extending distally from the proximal portion 18). The hub 24 may be attached to proximal portion 18.

The proximal portion 18 may have a lumen 22 defined therein. This, however, is not required and proximal portion 18 may be solid (e.g., a wire, a solid rod, etc.)

In some embodiments, lumen 22 may extend along the entire length of proximal portion 18. In other embodiments, lumen 22 may extend along only a portion of the length of proximal portion 18. In still other embodiments, proximal member 16 may be a hypotube and have a lumen extending along the entire length of proximal member 16.

In addition, proximal portion 18 may include both proximal and distal openings (e.g., positioned at the proximal and distal end of proximal portion 18) such that lumen 22 is "open" on both ends. Alternatively, one or both of the ends of proximal portion 18 may be closed or otherwise sealed. For example, the distal end of proximal portion 18 may be closed. In some of these and in other embodiments, proximal portion 18 may have an opening or port (not shown) formed in the wall of proximal portion 18 and spaced from the proximal and/or distal end of proximal portion 18. The port may or may not be in fluid communication with lumen 22.

A distal sheath 26 may be attached to proximal member 16. In some cases, the distal sheath 26 may be axially fixed to proximal member 16, but this is not required. Distal sheath 26 may have a lumen 28 formed therein. The distal sheath 26 may have a single lumen or two or more lumens. In general, lumen 28 (and/or the inner diameter of distal sheath 26) may be larger than lumen 22 (and/or the inner diameter of proximal portion 18) and may be larger than the outer diameter of proximal member 16.

A distance of an inner diameter of the lumen 28 may be any distance configured to facilitate the distal sheath 26 to traversing a patient's vasculature. In some examples, the distance of the inner diameter of the lumen 28 may be between 0.025 inches (0.635 millimeters) and about 0.090 inches (2.29 millimeters), between about 0.035 inches (0.889 millimeters) and about 0.080 inches (2.03 millimeters), between about 0.040 inches (1.02 millimeters) and about 0.075 inches (1.91 millimeters), and/or may be between other distances. Illustratively, the distance of the inner diameter of the lumen 28 may be about 0.046 inches (1.17 mm), about 0.047 inches (1.19 millimeters), about 0.051 inches (1.30 millimeters), about 0.052 inches (1.32 millimeters), about 0.056 inches (1.42 millimeters), about 0.057 inches (1.45 millimeters), about 0.062 inches (1.57 millimeters), about 0.063 inches (1.60 millimeters), about 0.071 inches (1.80 millimeter), about 0.072 inches (1.83 millimeters), and/or one or more other distances.

As used herein, the term diameter may refer to a line from one side of something to a second side of the something, wherein the line passes through a center point of the something. Illustratively, the something may be a cross-sectional shape of a square, a circle, a triangle, an oval, a rectangle, or other shape. With respect to proximal member 16 and/or distal sheath 26 that may not have a circular cross-sectional shape, the diameter of such shapes may be the largest cross-sectional dimension of proximal member 16 or distal sheath 26 taken from a cross-section transverse to a longitudinal dimension (e.g., to a direction of a longitudinal axis. Accordingly, lumen 28 may be sufficiently large so as to allow a therapeutic catheter (e.g., a delivery device, a balloon catheter, a stent delivery system, etc.) to pass therethrough. For example, when guide extension catheter 14 is positioned within guide catheter 10, the therapeutic catheter may extend within guide catheter 10 alongside proximal member 16 and through lumen 28 of distal sheath 26.

Distal sheath 26 may include a body portion 30. In at least some embodiments, body portion 30 may include one or more polymers including any of those disclosed herein. This may include the use of polymers with a differing durometer along the length of body portion 30. For example, a more proximal section of body portion 30 may include a polymer with a higher durometer and a more distal section of body portion 30 may include a polymer with a lower durometer. Portions of all of the length of body portion 30 may be loaded with or otherwise include a radiopaque material.

Body portion 30 may also include a reinforcement member 32, but this is not required. The form of reinforcement member 32 may vary. For example, reinforcement member 32 may include a braid, coil, mesh, rings, segments, fibers or interstitial arrays of fibers, or the like.

An inner layer or liner 34 may be disposed along an inner surface of body portion 30, but this is not required. The form of liner 34 may vary. For example, liner 34 may be a lubricious liner or otherwise include a lubricious material such as polytetrafluoroethylene.

A tip member 36 may be attached to body portion 30, for example at a distal end of body portion 30, but this is not required. In some embodiments, tip member 36 may be a single layer of material. Alternatively, tip member 36 may include an outer layer 38 and an inner layer 40. Outer layer 38 and inner layer 40 may be formed from the same material. In some of these embodiments, outer layer 38 and inner layer 40 may include the same polymeric material and each may be loaded with the same or different radiopaque materials. For example, inner layer 40 may include a polyether block amide loaded with approximately 75-95% (e.g., about 90%) by weight tungsten and outer layer 38 may include a polyether block amide loaded with approximately 30-50% (e.g., 40%) by weight bismuth subcarbonate. These are just examples. In other embodiments, outer layer 38 and inner layer 40 may be made from different materials.

Distal sheath 26 may be attached to extension portion 20 of proximal member 16. The arrangement and/or configuration of the attachment between extension portion 20 and distal sheath 26 may vary. For example, distal sheath 26 may have an opening or lumen formed in a tube wall thereof and extension portion 20 may be disposed within the opening. This may include stamping, flattening, necking, skiving, and/or pinching down extension portion 20 and inserting the necked down portion into the opening. In some embodiments, inserting extension portion 20 into the opening may secure proximal member 16 to distal sheath 26 via a mechanical bond. In some of these and in other embodiments, additional and/or alternative bonding may be utilized including those bonding mechanisms commonly used for medical devices. Some example bonding mechanisms include adhesive bonding, welding, thermal bonding, brazing, metallurgical stamping, pressing etc. Other attachment mechanisms are also contemplated for attaching the proximal member 16 to distal sheath 26 including direct bonding (e.g., adhesive bonding, thermal bonding, welding, brazing, injection molding, 3D printing and bonding, overmolding, casting, sintering polymer/metal composites, etc.) and bonding that is facilitated by a third component such as a metal or polymer collar member 42 that may be bonded between the extension portion 20 and distal sheath 26.

Guide extension catheter 14 may also include a number of coatings that may, for example, reduce friction. For example, proximal member 16 may have an inner and/or outer coating that includes a hydrophilic polymer that may reduce friction during tracking. An example coating may include BAYER CL-100, BIOSLIDE, NG-HPC, SLIP COAT, MDX, ZGLIDE, or the like. These are just examples. Other materials are contemplated including those disclosed herein.

Figure 4:
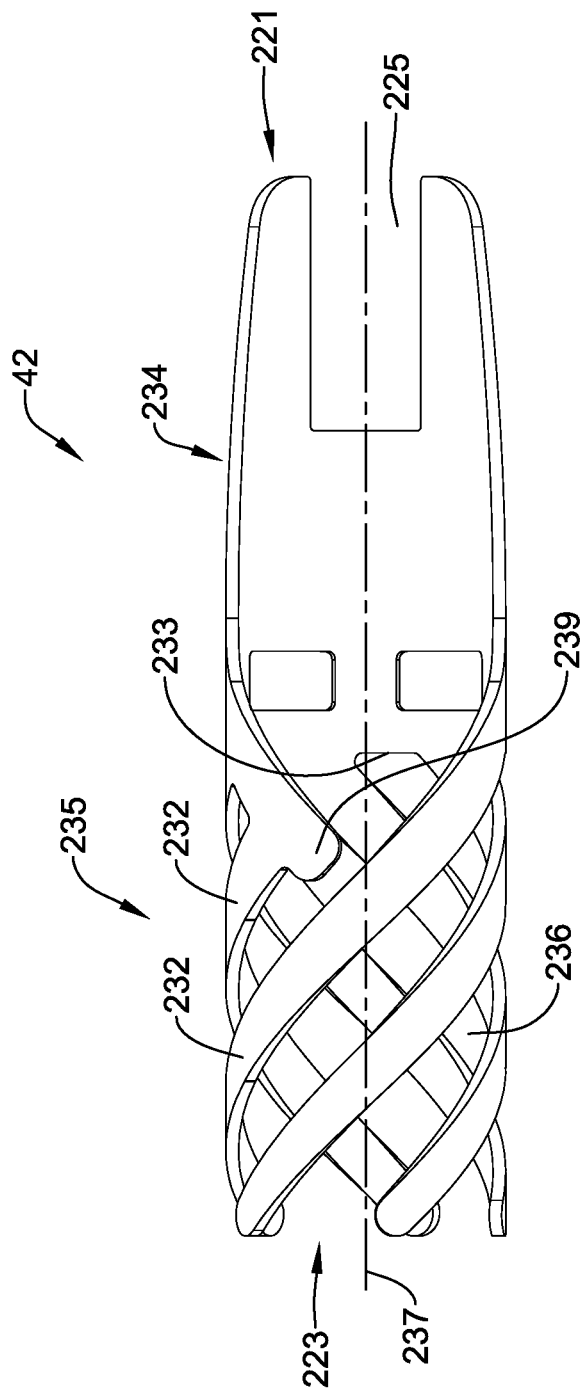
FIG. 4 is side view of an example guide extension catheter collar.

As discussed, some embodiments of guide extension catheter 14 may include collar member 42 connected between proximal member 16 and distal sheath 26, as illustrated in FIGS. 3 and 4. In some instances, collar member 42 may be sized to work with the guide catheter 10 or guide extension catheter 14 that have sizes between about 4 French to about 9 French. However, in other embodiments, collar member 42 may be sized differently to cooperate with guide catheters 10 and/or guide extension catheters 14 that are smaller than 4 French and larger than 9 French.

FIG. 4 is an illustrative perspective views of an example collar member 42 that may be used to facilitate bonding between an extension portion and a distal sheath of a guide extension catheter, such as extension portion 20 and distal sheath 26 of guide extension catheter 14 described with respect to FIGS. 3 and 4. Additionally, other configurations of collar members are contemplated.

FIG. 4 depicts collar member 42 including proximal end 221 and distal end 223. Collar member 42 comprises base portion 234 and a distally extending portion 235.

In some instances, distally extending portion 235 may comprise ribs 232 which extend distally away from base portion 234. As shown in FIG. 4, ribs 232 may extend from base portion 234 all the way to distal end 223 of collar member 42. However, in other instances this does not need to be the case. One or more of ribs 232 may not extend all the way to distal end 223 of collar member 42. Additionally, ribs 232 are just one example of distally extending portion 235.

Collar member 42 may additionally include slot 225. To attach collar member 42 to a member, such as proximal member 16 of FIG. 3, a distal end of the member may be inserted into slot 225 and may be bonded to collar member 42 by bonding mechanisms commonly used for medical devices. Some example bonding mechanisms include adhesive bonding, welding, thermal bonding, brazing, etc.

Distally extending portion 235 may be attached to a sheath, such as the distal sheath 26 of FIG. 3, in a similar manner to how proximal member 16 may be attached to collar member 42. In other instances, distally extending portion 235 may be inserted into one end of the sheath, and both the distally extending portion 235 and the sheath may be heated. This heat may cause the material of the sheath to melt and flow into and/or around distally extending portion 235. When the heat is removed, the melted material may solidify, thereby bonding the sheath to distally extending portion 235.

In instances where distally extending portion 235 comprises ribs 232, ribs 232 may extend distally away from base portion 234, which is defined as the angle between top 233 of base portion 234 and rib 232. In one example, the angle at which ribs 232 extend distally away from the top 233 of the base portion 234 may be 45 degrees. However, illustratively, the angle may have any value between about 15 degrees and about 75 degrees. In some more specific instances, the angle at which ribs 232 extend away from the top 233 of the base portion 234 may have any value between about 30 degrees and about 60 degrees.

Although FIG. 4 depicts collar member 42 having five ribs 232, in other instances, collar member 42 may have a different number of ribs 232. For example, collar member 42 may have between about one rib 232 and about ten ribs 232. In more specific instances, collar member 42 may have between about four ribs 232 and about seven ribs 232. In other instances, the collar member 42 may have no ribs.

In at least some instances, ribs 232 may extend distally away from base portion 234 in a twisting manner. As one example, ribs 232 may have a helical twist and extend distally away from base portion 234 in a helical manner. Although shown as extending in a generally clock-wise helical manner when viewing collar member 42 from proximal end 221, in other instances, the helical twist may be counter-clockwise.

In at least some instances, each of ribs 232 may extend helically around a longitudinal axis of the collar member 42 at least 90 degrees. In other instances, each of ribs 232 may extend helically around the longitudinal axis about 180 degrees, about 360 degrees, or anywhere between 90 degrees and 360 degrees. In still other instances, each of ribs 232 may helically twist around the longitudinal axis multiple times as ribs 232 extend distally from base portion 234.

In still other instances, ribs 232 may not extend distally away from base portion 234 in a twisting manner at all. For instance, ribs 232 may extend distally away from base portion 234 in a straight manner.

In some additional instances, ribs 232 may have a wavy or sinusoidal shape. For instance, ribs 232 may extend generally distally away from base portion 234 in a straight fashion, except ribs 232 may curve back and forth transversely to a longitudinal axis. Or, in other instances, ribs 232 may undulate up and down in a manner parallel to a longitudinal axis of the collar member 42.

In at least some embodiments, ribs 232 may have one or more connecting members disposed generally transverse to the direction of ribs 232, connecting ribs 232 together. The connecting members may simply be thin portions of collar member 42 left during the processing to form ribs 232. These connecting members may be relatively thin compared to the width of ribs 232.

FIG. 4 additionally depicts ribs 232 extending away from the top 233 of base portion 234 a distance. In different instances, the distance may be any value between about 0.05 inches (1.27 mm) and about 0.5 inches (12.7 mm). Additionally, although all of ribs 232 are depicted as extending distally away from the top 233 of base portion 234 the same distance, in other instances, each of ribs 232 may extend distally away from the top 233 of the base portion 234 different distances, or groups of one or more ribs 232 may extend distally away from the top 233 of the base portion 234 different distances. In at least some instances where ribs 232 extend helically around longitudinal axis 237, ribs 232 may extend away from base portion 234 a distance such that at least two separate ribs cross a longitudinal axis of the collar member 42. In others of these embodiments, at least three separate ribs may cross the longitudinal axis of the collar member 42. In still other embodiments, based on the distance ribs 232 extend distally away from base portion 234, every one of ribs 232 may cross the longitudinal axis of the collar member 42.

In some embodiments, collar member 42 may include channels 236 defined by distally extending portion 235. For instance, collar member 42 may be made from a hollow tube. The hollow tube may be machined, laser cut, or otherwise processed to remove material to define channels 236 extending along the longitudinal axis for at least a portion of collar member 42. Channels 236 may be angled with respect to the longitudinal axis at an angle similar to how ribs 232 may be angled with respect to base portion 234. For instance, channels 236 may be angled with respect to a longitudinal axis of the collar member 42 between about 15 degrees and about 75 degrees, between about 30 degrees and about 60 degrees, or about 45 degrees. Channels 236 may have one closed end, for instance where each channel 236 meets the top 233 of the base portion 234, and one open end, for instance at distal end 223. Additionally, different instances of collar member 42 may include varying numbers of channels 236, for instance any number between about two and ten channels, or between about four channels and seven channels.

As illustrated in FIG. 4, in some instances, collar member 42 may additionally include angled extension 239. Angled extension 239 may extend distally away from base portion 234 in a similar manner to ribs 232. However, angled extension 239 may extend in a direction generally transverse to ribs 232. For example, as ribs 232 are depicted extending helically in a clock-wise manner, angled extension 239 may extend in a generally counter-clockwise manner. As depicted in FIG. 4, angled extension 239 may form an angle with a top 233 of the base portion 234 (e.g., a distal-most edge of base portion 234). In the example of FIG. 4, the angled extension 233 extends at an angle of 45 degrees. However, in different embodiments, the angle of angled extension 239 extending away from the top 233 of the base portion 234 may have any value between about 15 degrees and 75 degrees. In more specific instances, the angle may have any value between about 30 degrees and 60 degrees. In some instances, the angle may have the same value as the angle at which ribs 232 extend away from the top 233 of the base portion 234, but this does not need to be true in all embodiments. Further, in at least some instances, one or more of ribs 232 may extend from angled extension 239, as depicted in FIG. 4, but this does not need to be the case in all embodiments.

Figure 5:
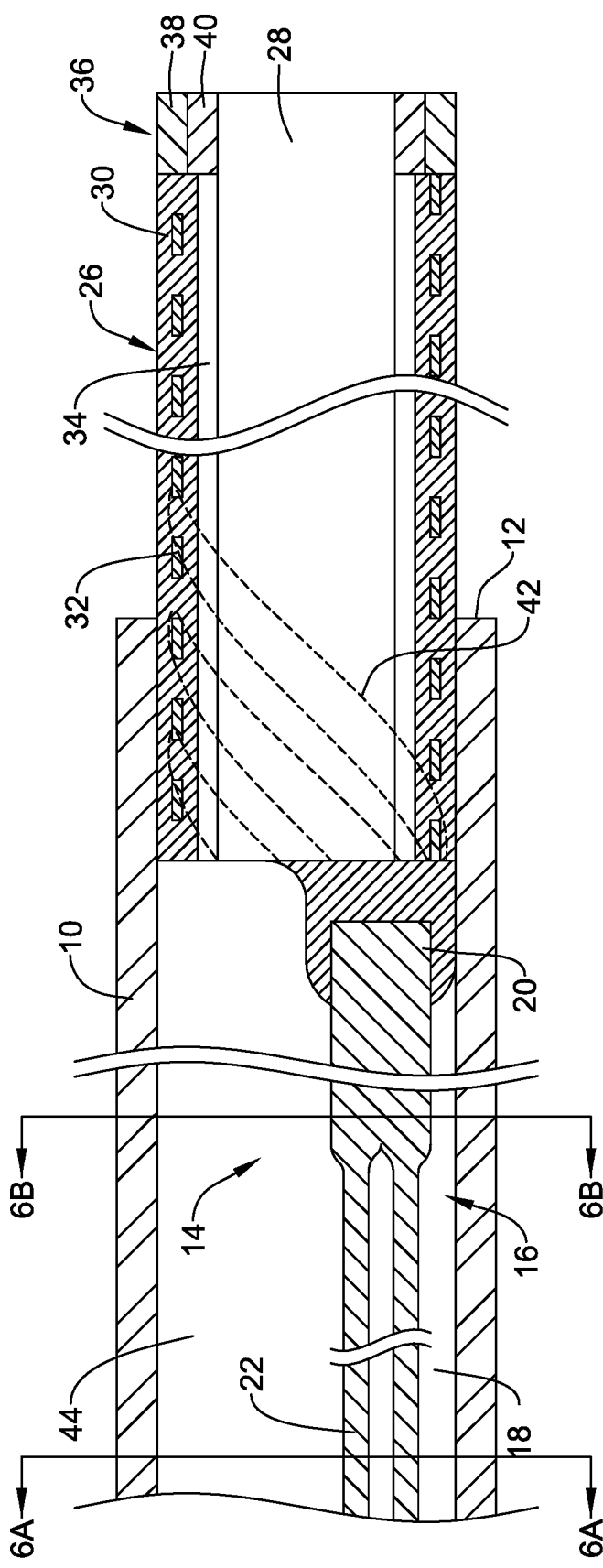
FIG. 5 is a cross-sectional side view of an example guide extension catheter and an example guide catheter.

FIG. 5 illustrates guide extension catheter 14 disposed within guide catheter 10 (e.g., disposed within a lumen 44 defined within guide catheter 10). As shown, distal sheath 26 may be arranged to extend distally out from distal end 12 of guide catheter 10. When so arranged, distal sheath 26 may engage the ostium O and/or extend within a portion of the coronary artery CA to help maintain the position of guide catheter 10 and improve access to the coronary artery CA. Proximal member 16 may be designed to be sufficiently small (while still being sufficiently sized and configured for pushability) so as to take up relatively little space within the interior or lumen 44 of guide catheter 10 and extend exterior a patient's vasculature when the distal sheath is at a target location. Accordingly, the use of guide extension catheter 14 allows for a therapeutic catheter or medical device to be advanced through guide catheter 10 in order to reach the desired target location for the intervention. In some embodiments, proximal member 16 may contact the inner wall surface of guide catheter 10, which may provide even more space.

Figure 6B:
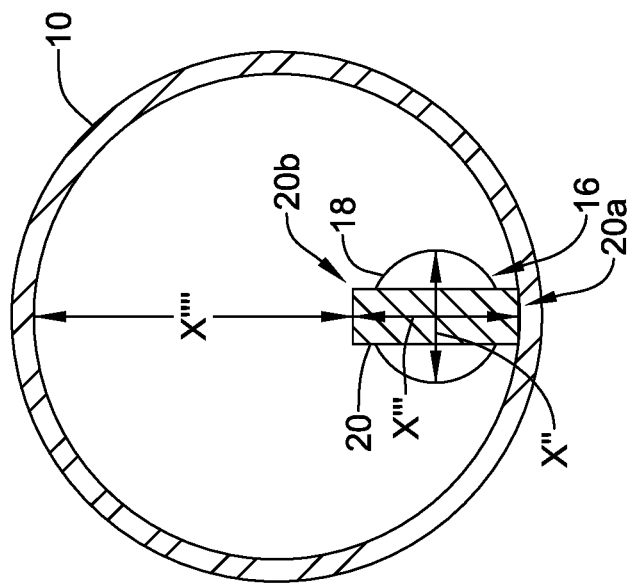
FIG. 6B is a schematic cross-sectional view of the guide extension catheter and guide catheter of FIG. 5 taken along line 6B-6B.
Figure 6A:
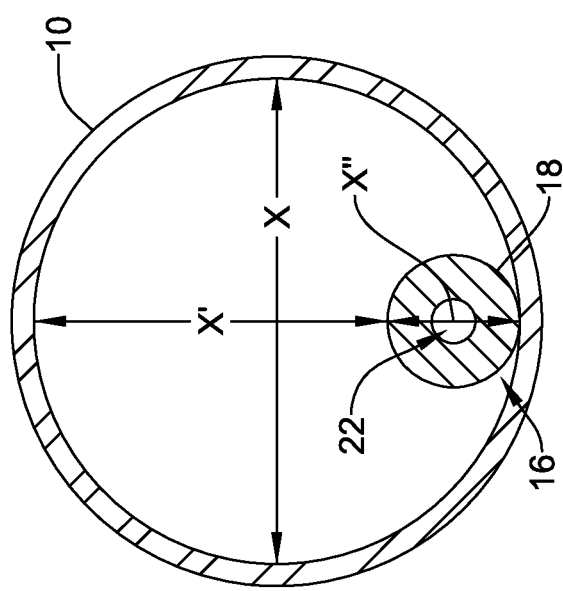
FIG. 6A is a schematic cross-sectional view of the guide extension catheter and guide catheter of FIG. 5 taken along line 6A-6A.

FIGS. 6A and 6B are cross-sectional views taken along line 6A-6A and line 6B-6B in FIG. 5, respectively. Generally, FIGS. 6A and 6B depict example relative spacing within guide catheter 10 with respect to proximal member 16 of the guide extension catheter 14 at lines 6A-6A and 6B-6B of FIG. 5.

As can be seen in FIG. 6A, line X may represent an inner diameter of the guide catheter 10, line X' may represent a distance from an outer surface of the proximal portion 18 of the proximal member 16 to an inner surface of the guide catheter 10, and line X" may represent an outer diameter of the proximal portion 18 of the proximal member 16. The line X' may represent a maximum possible diameter for a delivery device and/or a combined delivery device and medical device that may travel through the guide catheter 10 while the guide extension catheter 14 is inserted therein.

Line X may have any length dimension. For example, line X may have a length dimension within a range of about 0.040 inches to about 0.100 inches, about 0.050 inches to about 0.090 inches, about 0.060 inches to about 0.080 inches, and/or within one or more other ranges. In one illustrative example, line X may have a length dimension of about 0.070 inches.

Line X' may have any length dimension. For example, line X' may have a length dimension within a range of about 0.0200 inches to about 0.0830 inches, about 0.0305 inches to about 0.0725 inches, about 0.0410 inches to about 0.0620 inches, and/or within one or more other ranges. In one illustrative example, line X' may have a length dimension of about 0.0515 inches.

Line X" may have any length dimension. For example, line X" may have a length dimension within a range of about 0.0170 inches to about 0.0200 inches, about 0.0175 inches to about 0.0195 inches, about 0.0180 inches to about 0.0190 inches, and/or within one or more other ranges. In one illustrative example, line X" may have a length dimension of about 0.0185 inches.

In some cases the extension portion 20 of the proximal member 16 may twist or shift within the guide catheter 10 as it extends proximally from a distal end thereof as seen in FIGS. 5 and 6B. When the extension portion 20 twists or shifts within the guide catheter 10, a maximum space for a delivery device or other device to travel through the guide catheter 10 may be reduced. As can be seen in FIG. 6B, line X''' represents a width of extension portion 20 of the proximal member 16 and line X'''' represents a distance from an outer surface of the extension portion 20 to an inner surface of the guide catheter 10. The line X'''' may represent a maximum possible diameter for a delivery device and/or combination of a delivery device and a medical device if the medical device need to cross from side 20b to side 20a of the extension portion 20 of the proximal member 16. The distance represented by line X'''' as shown in FIG. 6B is less than the distance represented by line X' in FIG. 6A, but this is not required.

Line X''' may have any length dimension. Although line X''' is depicted in FIG. 6B has having a length greater than line X'', line X''' may alternatively have a length equal to or less than a length X''. Example length dimensions of line X''' may be within a range of about 0.010 inches to about 0.040 inches, about 0.019 inches to about 0.035 inches, about 0.024 inches to about 0.030 inches, and/or within one or more other ranges. In one illustrative example, line X''' may have a length dimension of about 0.027 inches.

Line X'''' may have any length dimension. For example, line X'''' may have a length dimension within a range of about 0.010 inches to about 0.090 inches, about 0.020 inches to about 0.071 inches, about 0.030 inches to about 0.056 inches, and/or within one or more other ranges. In one illustrative example, line X'''' may have a length dimension of about 0.043 inches.

In practice, a guide wire 50 may be thread through vasculature of a patient to a target location and the guide catheter 10 may be threaded through the patient's vasculature over the guide wire 50. Then, the guide extension catheter 14 may be threaded through the guide catheter 10 to the target location or at least a location distal of a distal end of the guide extension catheter 14. Once the guide extension catheter 14 is positioned, a delivery device and/or a medical device may be inserted and/or delivered through the guide catheter 10 and the guide extension catheter 14.

Figure 7:
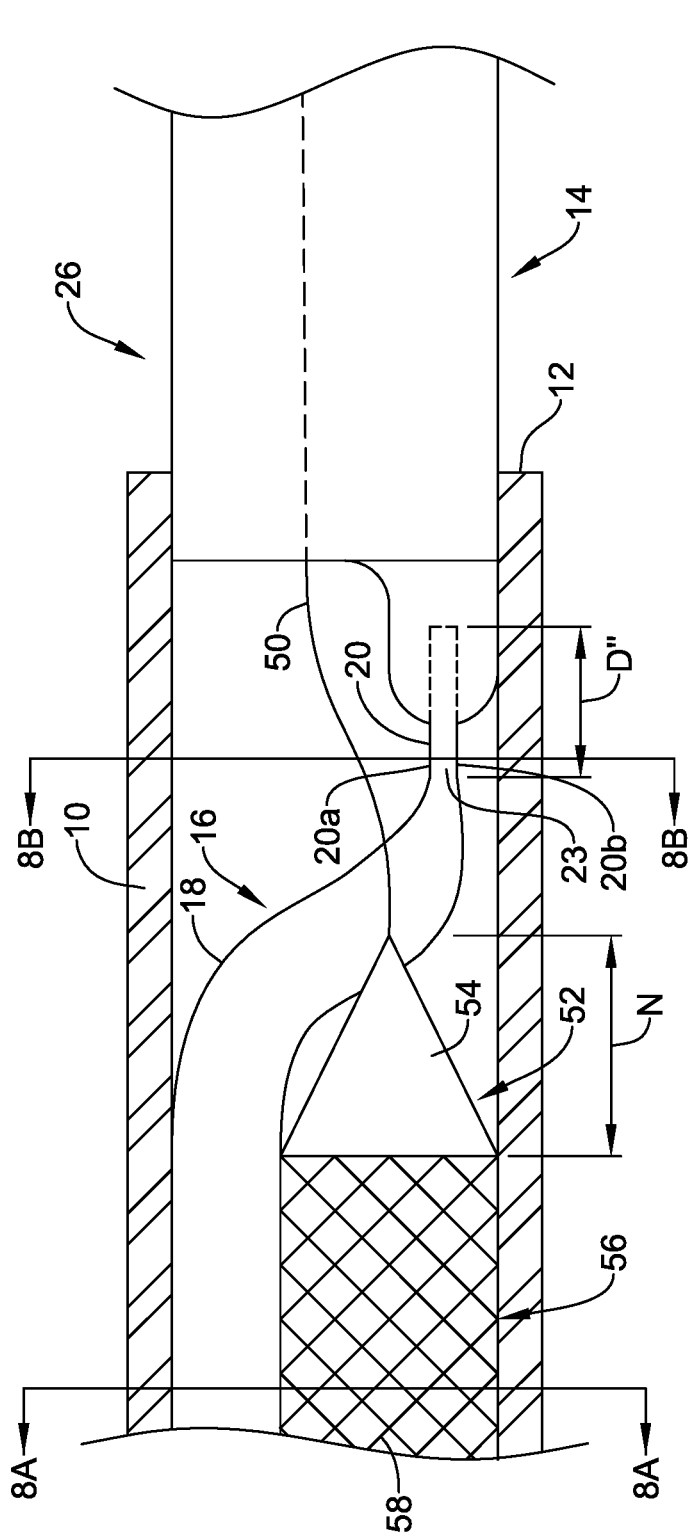
FIG. 7 is a schematic partial cross-sectional view of an example guide extension catheter, an example guide catheter, and an example delivery device.

FIG. 7 depicts the guide extension catheter 14 and a delivery device 52 (e.g., a stent delivery catheter, balloon catheter, and/or other delivery device) with a medical device 58 (e.g., a stent or other medical device) thereon inserted into the guide catheter 10. The delivery device 52 may be threaded over the guide wire 50, but this is not required.

As shown in FIG. 7, the guide extension catheter 14 may have the extension portion 20 having a flattened region 23 with a length D'' and the delivery device 52 have a nose 54 that has a length N. The delivery device 52 may include a medical device location 56 carrying thereon and/or enclosing therein the medical device 58, such as a stent as shown in FIG. 7. Delivery devices other than delivery device 52 are contemplated.

In operation, the proximal member 16 of the guide extension catheter 14 be flexible and thus, may be at different radial locations within the guide catheter 10 at different axial locations along a length of the proximal member 16, as shown in FIG. 7. As a result, the delivery device 52, for example, may move along various sides of the proximal member 16 as it is inserted through the guide catheter 10 and as the delivery device 52 approaches a proximal end of the distal sheath 26, the delivery device may be on an opposite side of the proximal member 16 than a side on which the delivery device 52 needs to be to be inserted into the lumen 28 of the distal sheath 26. Such a situation is depicted in FIG. 7, where the delivery device 52 may be approaching the extension portion 20 of the proximal member 16 on side 20b of the extension portion when it will need to be on side 20a of the extension portion 20 to be inserted into and/or through lumen 28 of the distal sheath 26.

Figure 8B:
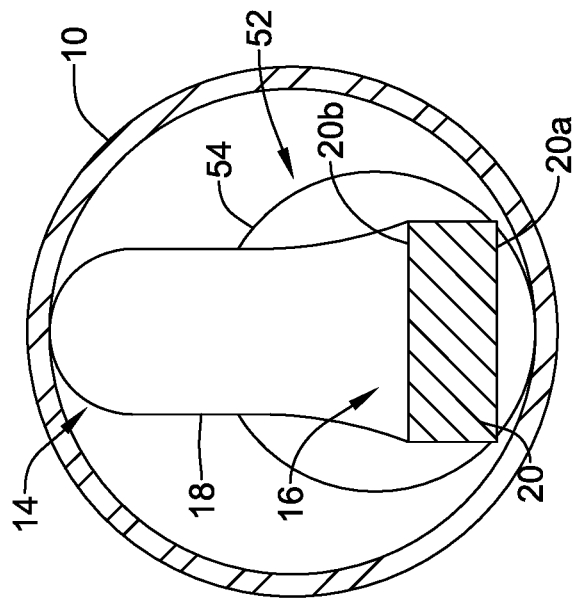
FIG. 8B is a schematic cross-sectional view of the guide extension catheter, guide catheter, and delivery device of FIG. 7 taken along line 8B-8B.
Figure 8A:
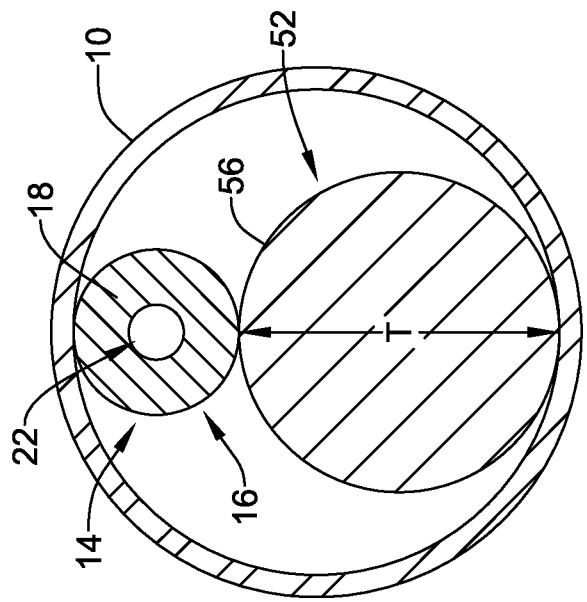
FIG. 8A is a schematic cross-sectional view of the guide extension catheter, guide catheter, and delivery device of FIG. 7 taken along line 8A-8A.

FIG. 8A depicts a cross-sectional view of the guide extension catheter 14 and delivery device 52 inserted into the guide catheter 10 taken along line 8A-8A in FIG. 7. In FIG. 8A, the medical device 58 has been omitted for clarity purposes. In FIG. 8A, the delivery device 52 may have a cross-sectional diameter T at the medical device location 56 or other location along the delivery device 52, which may be less than a distance of line X' extending from an outer surface of proximal portion 18 of the proximal member 16 to an inner surface of the guide catheter 10.

FIG. 8B depicts a cross-sectional view of the guide extension catheter 14 and delivery device inserted into the guide catheter 10 taken along line 8B-8B in FIG. 7. In FIG. 8B, the guide wire 50 and the medical device 58 have been omitted for clarity purposes. As shown in FIGS. 7 and 8B, the delivery device 52 may be positioned on a side (e.g., an outer facing side) of the proximal member 16 that is opposite a side (e.g., an inner facing side) on which the delivery device 52 may need to be to be inserted into and/or through the lumen 28 of the distal sheath 26. For example, as the delivery device 52 of FIGS. 7 and 8B is advanced distally, the delivery device 52 may advance along side 20b of the extension portion 20 of the proximal member 16. However, to advance into and/or through the lumen 28 of the distal sheath 26, the delivery device 52 may need to be on side 20a of the extension portion 20 of the proximal member 16.

When the delivery device 52 or other device is advanced within the guide catheter 10 along an outer facing side of the proximal member 16 of the guide extension catheter 14, the delivery device 52 may need to switch to an inner facing side of the proximal member 16. The do this, the delivery device 52 must switch sides of the proximal member at a location where a diameter T is less than a distance from an outer surface of the proximal member 16 to an inner surface of the guide catheter 10 (e.g., a distance of line X' or line X''''). As the diameter T may be greater than a distance of line X'''' between an outer surface of the extension portion 20 and an inner surface of the guide catheter 10, the delivery device 52 may need to switch sides or begin switching sides at a longitudinal position within the guide catheter 10 that is proximal of the extension portion 20 or is proximal at least a widest portion of the extension portion 20 or a portion of the extension portion 20 that is wider than a diameter of the proximal portion 18 of the proximal member 16.

If the delivery device 52 or other device having a diameter T is allowed to advance to a position on outer facing side 20b of the extension portion 20 of the proximal member 16, the delivery device 52 may get tangled between the proximal member 16 and the guide catheter. As a result, a physician may be required to apply undue push, pull, and/or rotational forces to the delivery device 52 to align or re-align the delivery device 52 (e.g., the medical device location 56 of the delivery device 52) with the lumen 28 of the distal sheath 26. These undue forces may cause physical damage to a patient that may not otherwise be applied to a patient if the delivery device 52 had not been tangled or caught on the proximal member 16. Additionally or alternatively, the undue forces may cause movement of the distal end of the guide catheter 10 and/or guide extension catheter 14 away from a desired position.

FIGS. 9-12B illustrate example guide extension catheters 14 or portions thereof that may be configured to allow a delivery device to extend along a surface of the extension portion 20 of the proximal member 16 and align with and/or extend through the lumen 28 of the distal sheath 26. Although example guide extension catheters 14 may be depicted, other guide extension catheters 14 consistent with this specification may be utilized to allow a delivery device to extend along a surface of the extension portion 20 and align with or extend through the lumen 28 of the distal sheath 26.

Figure 9A:
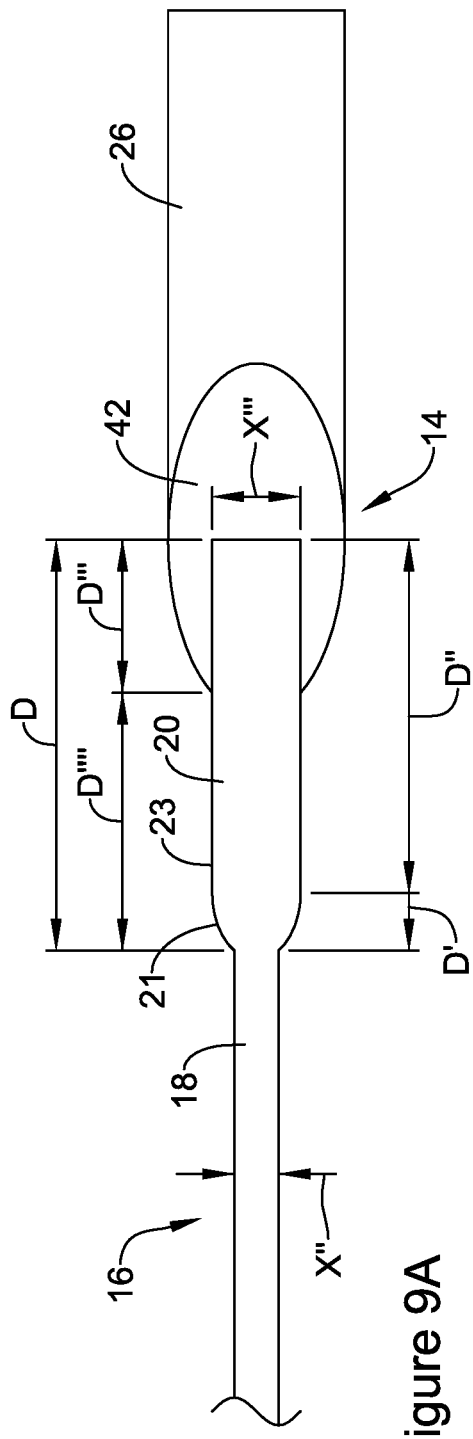
FIG. 9A is a top view of an example guide extension catheter.
Figure 9B:
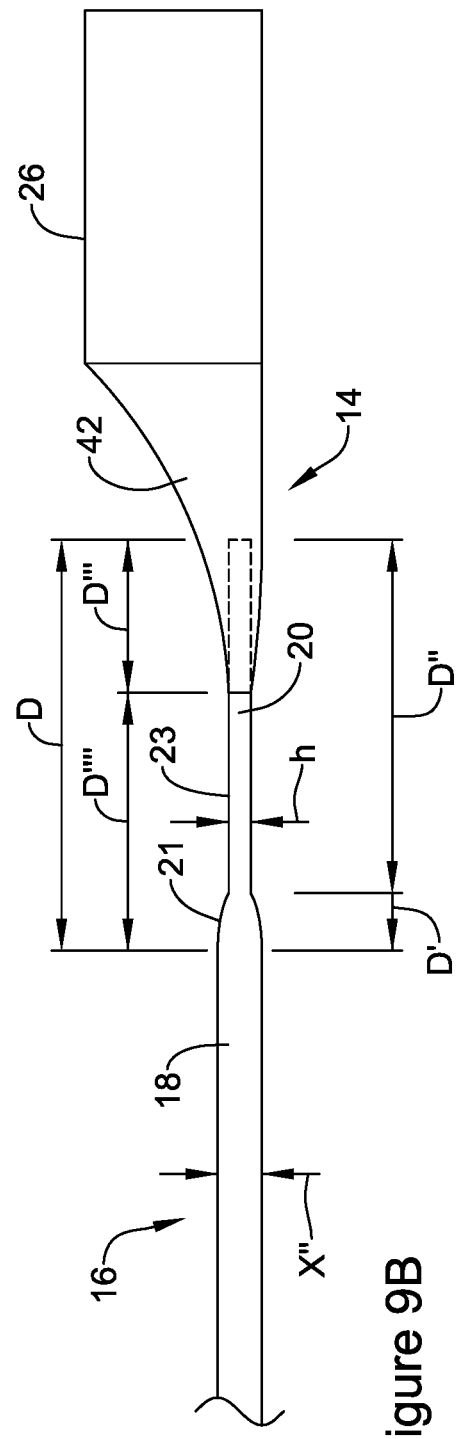
FIG. 9B is a side view of the guide extension catheter of FIG. 9A.

As shown in FIGS. 9A and 9B, the extension portion may include a transition region 21 and the flattened region 23. In some cases, the flattened region 23 may have a width equal to a length of line X'''. Additionally or alternatively, a width of the flattened region 23 may be greater than a diameter of the proximal portion 18 (e.g., length of line X'') and/or less than an outer diameter of the distal sheath 26. Further, a height, h, of the flattened region 23 (e.g., where height may be perpendicular to the width) may be within a range of about 0.001 to 0.020 inches or about 0.005 to 0.015 inches. In one illustrative example, the height, h, of the flattened region 23 may be about 0.010 inches.

The transition region 21 may be at a location of the proximal member 16 that transitions from the proximal portion 18 of the proximal member 16 to a flattened or widened region of the proximal member 16. In one example, the transition region 21 may taper from the flattened or widened region in a proximal direction to the proximal portion 18 of the proximal member 16.

The flattened or widened region (e.g., flattened region 23) of the proximal member 16 may be configured for attachment to the collar member 42 and/or the distal sheath 26. Additionally or alternatively, the flattened or widened region of the extension portion 20 may facilitate grasping of the proximal member 16 during manufacturing of the guide extension catheter 14 (e.g., for grasping while connecting the proximal member 16 to the collar member 42 or the distal sheath 26 and/or for grasping at other times).

In some instances, the transition region 21 may extend a length D' and flattened region 23 may extend a length D''. In FIGS. 9A and 9B, a sum of lengths D''' and D'' may be a length D of the extension portion 20. Although length D' may be depicted as having a length less than length D'', length D' may be greater than length D''.

Figure 10A:
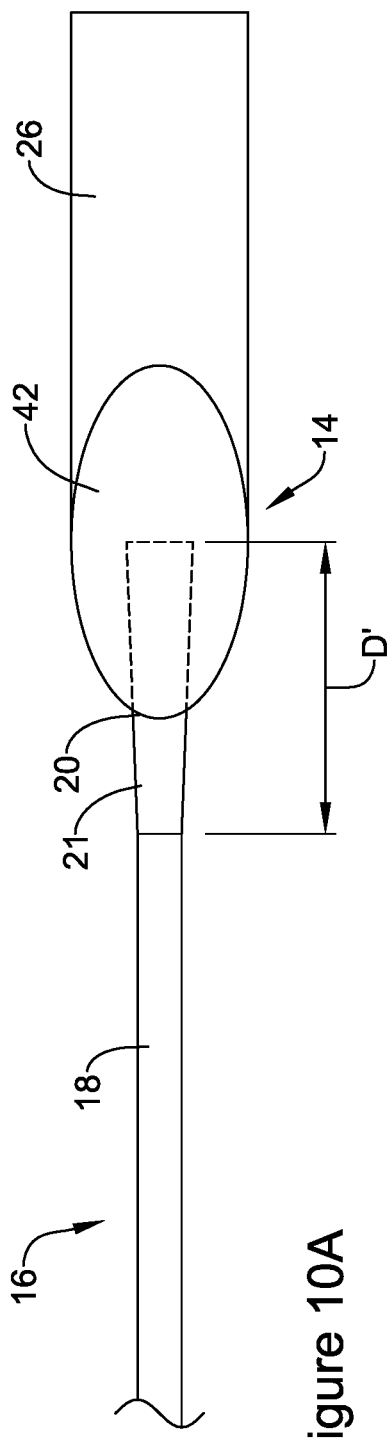
FIG. 10A is a top view of an example guide extension catheter.
Figure 10B:
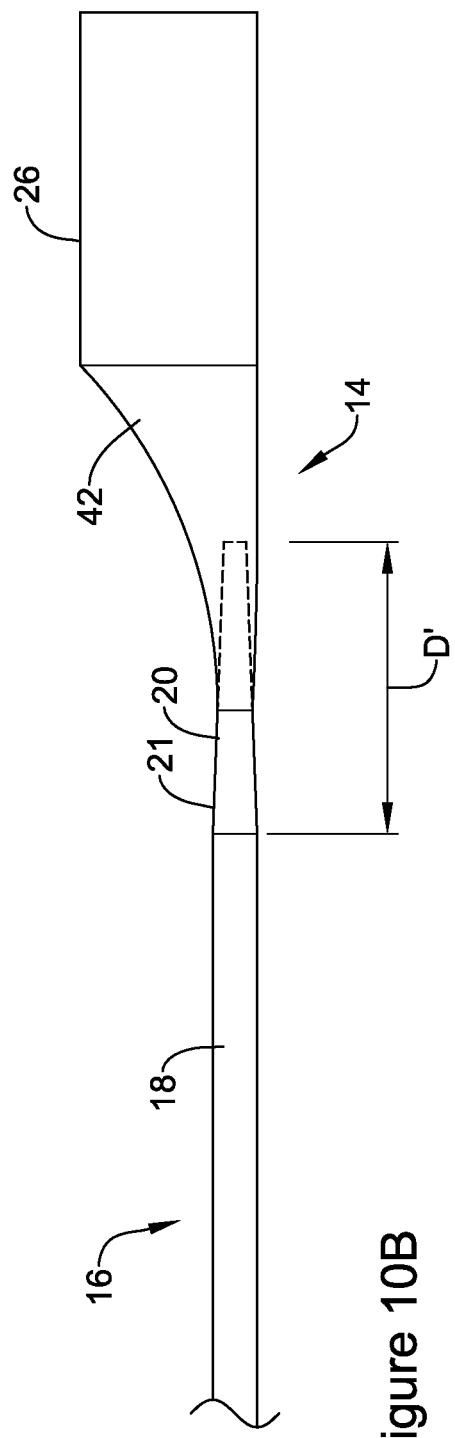
FIG. 10B is a side view of the guide extension catheter of FIG. 10A.

FIGS. 10A and 10B depict an additional instance of guide extension catheter 14 having the proximal member 16 with the extension portion 20. In FIGS. 10A and 10B, the extension portion 20 may include the transition region 21 that may extend an entire length of the extension portion 20. For example, the extension portion 20 may transition from the proximal portion 18 of the proximal member 16 to a distal end of the proximal member 16 and extend a total length D'. The total length D'' in FIGS. 10A and 10B may have similar dimensions to those of length D'' discussed below.

As shown in FIGS. 9A-10B and as discussed above, the extension portion 20 of the proximal member 16 may have a length D (or a length D' in the instance shown in FIGS. 10A and 10B). The length D may be a length extending from a distal end of the proximal member 16 to a location an axial location proximal of the distal end of the proximal member 16. The length D of the extension portion 20 may include the transition region 21, the flattened region 23, or both of the transition region 21 and the flattened region 23.

In some cases, as shown in FIGS. 9A and 9B for example, the length D may include a length D''' of the extension portion 20, where the length D''' may represent a length of the extension portion 20 that overlaps with and/or may be attached to the collar member 42 and/or the distal sheath 26. A length D'''' (length D minus length D''') of the extension portion 20 may be a length of the extension portion 20 extending proximally from a proximal end of the collar member 42. In one example, length D''' may be in the range of about zero (0) millimeters to three (3) millimeters, about one (1) millimeters to two (2) millimeters, or other distance. In one instance, about 1.5 millimeters of the extension portion 20 may overlap with the collar member 42 and about 1.5 millimeters of the extension portion 20 may extend proximally of a proximal end of the collar member 42 to facilitate grasping the proximal member 16 and attaching the proximal member 16 to the collar member 42.

Length D'' may have a length that is less than about nineteen (19) millimeters, less than about ten (10) millimeters, between about one (1) millimeter and ten (10) millimeters, between about zero (0) millimeters and six (6) millimeters, between about zero (0) millimeters and three (3) millimeters, between about zero (0) millimeters and one-point-five (1.5) millimeters, and/or a length D within one or more other ranges. In one instance, the length D'' may be about 6.35 millimeters. In another instance, the length D may be about three (3) millimeters. In yet a further instance, the length D'' may be one-point-five (1.5) millimeters. It has been found that a smaller length of the extension portion 20 may be desirable to prevent catching the delivery device 52 or other device on the extension portion 20, but that it may be desirable for the extension portion to have some length to facilitate grasping the proximal member during manufacturing and connecting the proximal member 16 to the collar member 42 and/or the distal sheath 26.

In some instances, length D'' may be configured to be a fractional distance of a distance of a length of the distal sheath 26, where the distance of the length of the distal sheath 26 is a distance from a proximal end of the distal sheath 26 to a distal end of the distal sheath 26. Where the length of the distal sheath 26 has a distance between about fifteen (15) centimeters and forty (40) centimeters or other length, for example, the length D'' of the extension portion 20 may be between about 0.375% and about 6.7% of the length of the distal sheath.

In some instances, distance of length D'' may be configured to be proportional to a distance of an inner diameter of the distal sheath 26, where the distance of the inner diameter of the distal sheath 26 is a minimum diameter of lumen 28 of the distal sheath 26. Where the distance of the inner diameter of the distal sheath 26 is between about 0.046 inches (e.g. 1.17 millimeters) and 0.072 inches (e.g., 1.83 millimeters), for example, the length D'' of the extension portion 20 may be between about 80% and about 855% of the length of the distal sheath. In some instances, length D'' may be configured to be shorter than a length N of the nose 54 of the delivery device 52 or other device, as shown in FIG. 7, but this is not required. Delivery devices 52 may include nose 54 that is configured to track along a guide wire (e.g., guide wire 50) or that may otherwise facilitate aligning the delivery device 52 (e.g., the medical device location 56 of the delivery device 52) with a lumen (e.g., lumen 28 of the distal sheath 26). In addition to length N, nose 54 may taper distally. The distal taper of the nose 54 may facilitate the aligning the delivery device 52 with a lumen.

In instances when the length N of the nose 54 is longer than the length D of the extension portion 20, the taper on the nose 54 of the delivery device 52 may facilitate aligning the delivery device with the lumen prior to the delivery device 52 catching on the proximal member 16. In one example, when a length N of the nose 54 of the delivery device 52 is longer than a length of the extension portion 20 extending proximal from a proximal end of the collar member 42 (e.g., D minus D'''), the taper of the nose 54 aligns the delivery device (e.g., the medical device location 56 on the delivery device 52) with the lumen 28 of the distal sheath 26 regardless of which side of the proximal member the delivery device 52 may be located as it approaches the extension portion 20 and/or prior to the reaching the extension portion 20.

Figure 11:
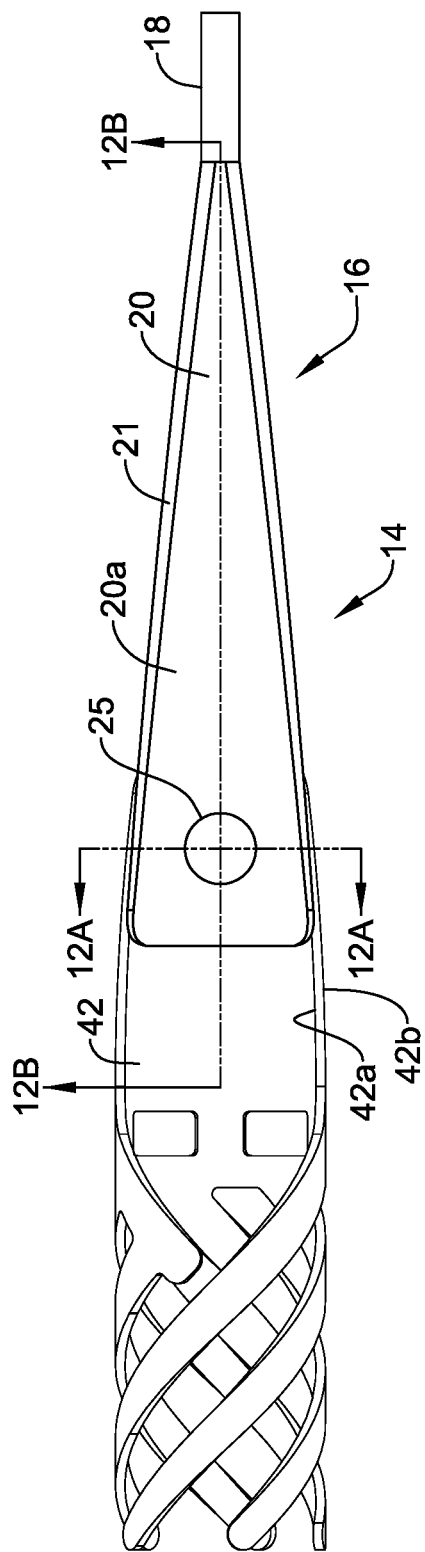
FIG. 11 is a top view of a proximal member and a collar of an example guide extension catheter.
Figure 12A:
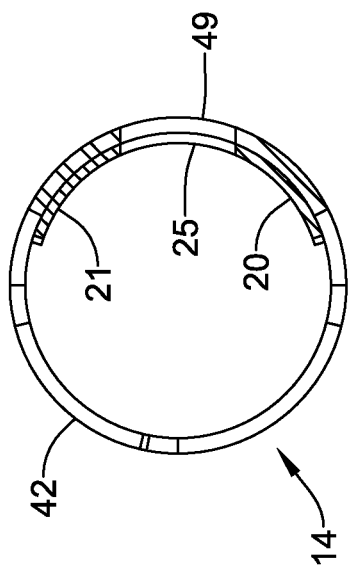
FIG. 12A is a schematic cross-sectional view of the proximal member and collar of FIG. 11 taken along line 12A-12A.
Figure 12B:
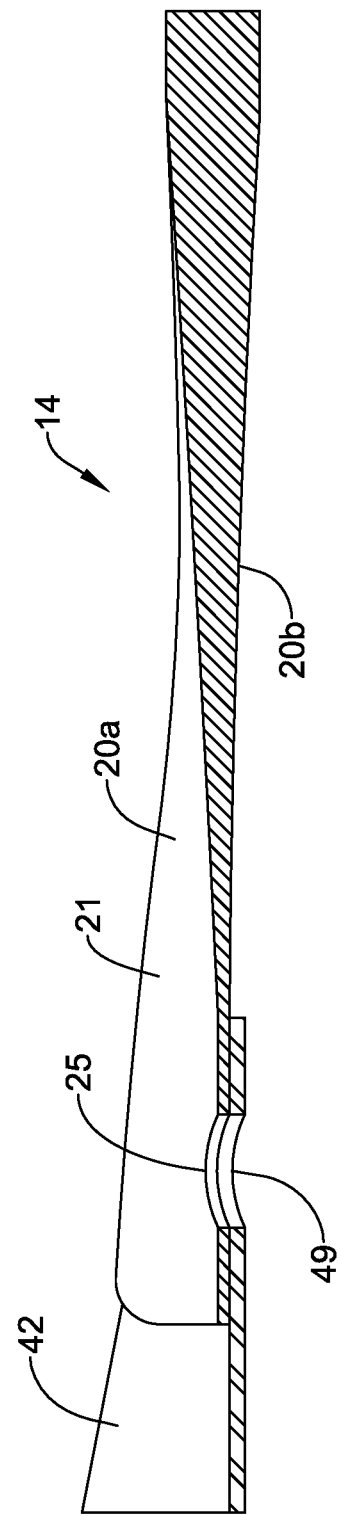
FIG. 12B is a schematic cross-sectional view of the proximal member and collar of FIG. 11 taken along line 12B-12B.

FIGS. 11-12B depict a further illustrative instance of the extension portion 20 of the proximal member 16. The extension portion 20 may have an arcuate and/or concave configuration and may taper from a distal end of the proximal member 16 to the proximal portion 18. An inner surface 20a and/or an outer surface 20b of the extension portion 20 may have a width and/or concavity configured to abut and/or engage an inner surface 42a and/or an outer surface 42b of the collar member 42. In one example, as shown in FIGS. 11-12B, the arcuate outer surface 20b of the extension portion 20 may be sized to receive and/or attached to an arcuate inner surface 42a of the collar member 42.

Further, during manufacturing of the guide extension catheter 14, a hole 25 in the extension portion 20 of the proximal member 16 and a hole 49 in the collar member 42 may be utilized to properly align the proximal member 16 with the collar member 42. FIG. 12A, which is a cross-sectional view taken along line 12A-12A of FIG. 11, depicts the axial alignment of the extension portion 20 and the collar member 42 facilitated by hole 25 and hole 49. FIG. 12B, which is a cross-sectional view taken along line 12B-12B of FIG. 11, depicts the longitudinal alignment of the extension portion 20 and the collar member 42 facilitated by hole 25 and hole 49. As may be seen in FIG. 12B, the extension portion 20 may overlap a distance D''' extending from a distal end of the proximal member 16 to a location proximal the distal end of the proximal member 16, as discussed above. Further, although holes 25 and 49 are described as being used to align the proximal member 16 and the collar member 42, this is not required and the holes 25, 49 may be eliminated, the holes 25, 49 may be used for other purposes, and/or other alignment features may be utilized.

Figure 13:
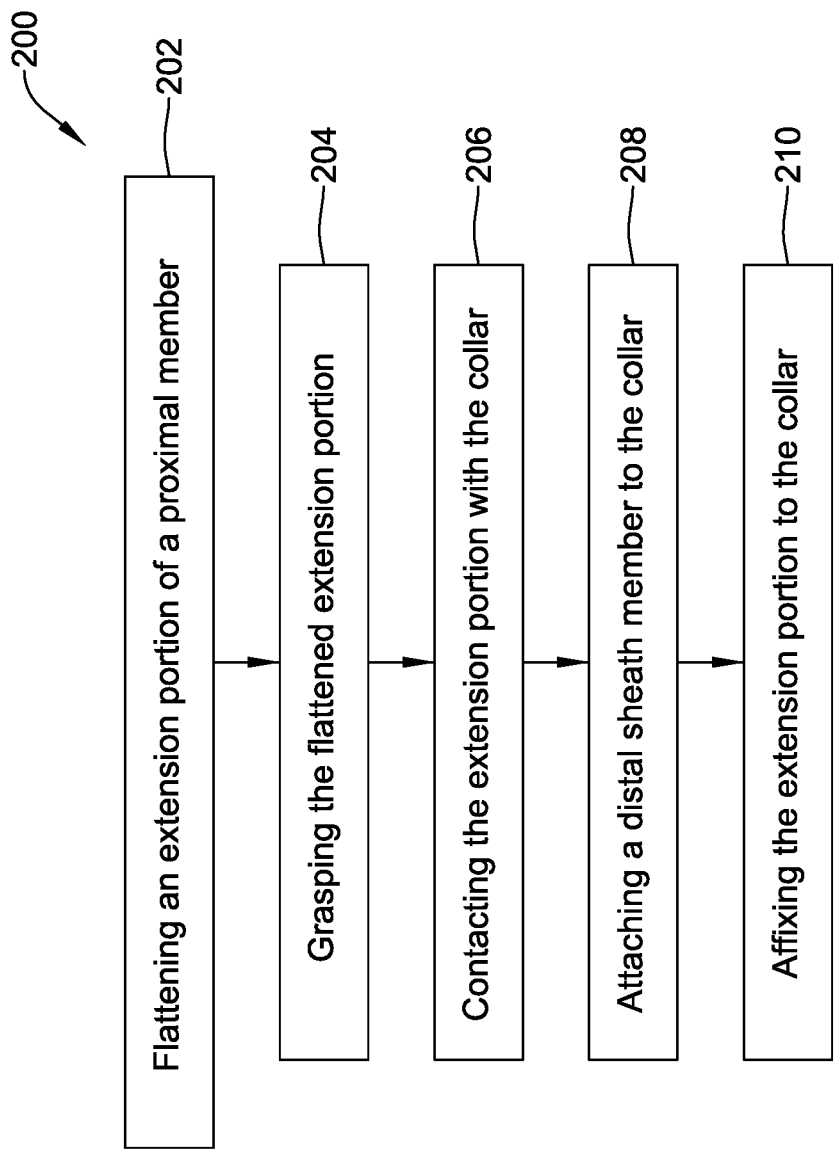
FIG. 13 is a schematic flow diagram illustrating a method of manufacturing a guide extension catheter.

The guide extension catheter 14 of the present disclosure may be manufactured in one or more manners. In one example method (200) of manufacturing the guide extension catheter 14 as shown in FIG. 13, a portion of a distal portion (e.g., the extension portion 20) of the proximal member 16 (e.g., a rod, wire, tube, or other elongated member) may be flattened (202). Flattening the distal portion of the proximal member 16 may include flattening a portion of the proximal member 16 that extends between the distal end of the proximal member 16 and a location less than nineteen (19) millimeters, less ten (10) millimeters, less than seven (7) millimeters, less than three millimeters, or at a different distance from the distal end of the proximal member 16. Flattening may include stamping, necking, skiving, and/or pinching down extension portion 20. As discussed above, the flattened portion of the extension portion 20 may be utilized for grasping and thus, the flattened or partially flattened extension portion 20 may be grasped (204) and the grasped extension portion 20 may be brought into contact with the collar member 42 (and/or the distal sheath 26) (206).

The distal sheath 26 may be attached to the collar member 42 through any connection technique (208). The distal sheath 26 may be attached to the collar member 42 at any time during the method of manufacturing (200). In one example, the distal sheath 26 may be attached to the collar member 42 before the extension portion 20 is affixed to the collar member 42 (as discussed below, as shown in FIG. 13). Alternatively, the distal sheath may be attached to the collar member 42 after the extension portion 20 is affixed to the collar member 42. Illustrative connection techniques may include direct bonding, such as but not limited to reflow bonding, adhesive bonding, thermal bonding, welding, 3D printing and bonding, overmolding, casting, sintering polymer/metal composites, and/or one or more other connection techniques.

When the extension portion 20 is in contact with the collar member 42, the extension portion 20 may be affixed to the collar member 42 (and/or the distal sheath 26) (210). In some instances, affixing the extension portion 20 to the collar and/or the distal sheath 26 may include one or more example bonding mechanisms including friction fit bonding, adhesive bonding, welding, thermal bonding, brazing, metallurgical stamping, pressing etc.

The materials that can be used for the various components of the guide extension catheters disclosed herein may vary. For simplicity purposes, the following discussion makes reference to proximal member 16, distal sheath 26, and collar member 42. However, this is not intended to limit the devices and methods described herein, as the discussion may be applied to other similar tubular members and collars and/or components of tubular members or collars or other devices disclosed herein.

In general, collar member 42 may be made from any suitable method, and may vary depending on the specific material or materials chosen for collar member 42. For example, if collar member 42 is made from a metal or metal alloy, collar member 42 may be formed by photo-etching, laser-cutting, micro-machining, 3D printing, sintering, rolled from flat sheet-stock. However, if collar member 42 is made from a polymer material, collar member 42 may be made through extrusion.

Proximal member 16, distal sheath 26, collar member 42 and/or other components of guide extension catheter 14 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of proximal member 16, distal sheath 26, and/or collar member 42 may also be loaded with, made of, or otherwise include a radiopaque material. Radiopaque materials are understood to be materials capable of producing a relatively bright image on a fluoroscopy screen or another imaging technique during a medical procedure. This relatively bright image aids the user of guide extension catheter 14 in determining its location. Some examples of radiopaque materials can include, but are not limited to, gold, platinum, palladium, tantalum, tungsten alloy, polymer material loaded with a radiopaque filler (e.g., barium sulfate, bismuth subcarbonate, etc.), and the like. Additionally, other radiopaque marker bands and/or coils may also be incorporated into the design of guide extension catheter 14 to achieve the same result.

In some embodiments, a degree of Magnetic Resonance Imaging (Mill) compatibility is imparted into guide extension catheter 14. For example, proximal member 16, distal sheath 26, and collar member 42, or portions thereof, may be made of a material that does not substantially distort the image and create substantial artifacts (i.e., gaps in the image). Certain ferromagnetic materials, for example, may not be suitable because they may create artifacts in an Mill image. Proximal member 16, distal sheath 26, and collar member 42, or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In at least some embodiments, a sheath or covering (not shown) may be disposed over portions or all of proximal member 16 and distal sheath 26 that may define a generally smooth outer surface for guide extension catheter 14. In other embodiments, however, such a sheath or covering may be absent from a portion of all of guide extension catheter 14, such that proximal member 16 and distal sheath 26 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guide extension catheter 14 (including, for example, the exterior surface of proximal member 16 and distal sheath 26) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of proximal member 16 and distal sheath 26, or other portions of guide extension catheter 14. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinyl alcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

What is claimed is:

1. A guide extension catheter, comprising:
   a proximal member having a rounded proximal portion with a proximal outer diameter, a flattened distal portion, and a transition portion extending from the rounded proximal portion to the flattened distal portion;
   a collar member attached to the flattened distal portion; and
   a distal sheath member attached to the collar member, the distal sheath member having a lumen and a distal outer diameter larger than the proximal outer diameter, and
   wherein the flattened distal portion has a length longer than the transition portion and has a constant width along the length of the flattened distal portion that is greater than the proximal outer diameter.

2. The guide extension catheter of claim 1, wherein the flattened distal portion has a constant height along a length of the flattened distal portion.

3. The guide extension catheter of claim 1, wherein the rounded proximal portion has a first cross-sectional area and the flattened distal portion has a second cross-sectional area that is equal to or less than the first cross-sectional area.

4. The guide extension catheter of claim 1, wherein the flattened distal portion extends proximally 1.5 millimeters from a distal end of the proximal member.

5. The guide extension catheter of claim 1, wherein the flattened distal portion and the transition portion extend less than 6.35 millimeters proximal of a distal end of the proximal member.

6. The guide extension catheter of claim 1, wherein the flattened distal portion and the transition portion extend less than 3 millimeters from a distal end of the proximal member.

7. The guide extension catheter of claim 1, wherein:
   the collar member comprises a base portion and one or more ribs connected to the base portion and extending distally away from the base portion; and
   the flattened distal portion of the proximal member is attached to the base portion of the collar member.

8. The guide extension catheter of claim 7, wherein the flattened distal portion and the transition portion extend less than 8.5 millimeters from a proximal end of the collar member.

9. The guide extension catheter of claim 7, wherein the flattened distal portion has an arcuate cross-section that mates with the arcuate cross-section of the base portion.

10. The guide extension catheter of claim 1, wherein the proximal member is solid.

11. The guide extension catheter of claim 1, wherein the transition portion includes a taper.

12. A medical treatment delivery system, the system comprising:
- a delivery device comprising a nose extending proximally from a distal end of the delivery device and a medical device location extending proximal from a proximal end of the nose, wherein the nose has a distal end with a length extending between the proximal end and the distal end of the nose;
- a guide extension catheter comprising:
  - a proximal member having a rounded proximal portion with a proximal outer diameter, a flattened distal portion, and a transition portion extending from the rounded proximal portion to the flattened distal portion;
  - a collar member attached to the flattened distal portion; and
  - a distal sheath member attached to the collar member, the distal sheath member having a lumen and a distal outer diameter larger than the proximal outer diameter, and
- wherein the flattened distal portion has a length longer than the transition portion and has a constant width along the length of the flattened distal portion that is greater than the proximal outer diameter.

13. The system of claim 12, wherein the nose has a length that is greater than the length of the flattened distal portion.

14. The system of claim 12, wherein the delivery device is a stent delivery catheter and the medical device location is configured to receive a stent.

15. The system of claim 12, wherein the delivery device is a balloon catheter and the medical device location includes a balloon.

16. The system of claim 12, wherein the proximal member is solid.

17. The system of claim 12, wherein the transition portion includes a taper.

* * * * *